(12) United States Patent
Knappe et al.

(10) Patent No.: US 8,168,162 B2
(45) Date of Patent: May 1, 2012

(54) STYLING AGENTS GIVING AN HIGH DEGREE OF HOLD

(75) Inventors: Thorsten Knappe, Schenefeld (DE); René Scheffler, Ellerau (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 437 days.

(21) Appl. No.: 12/442,561

(22) PCT Filed: Aug. 16, 2007

(86) PCT No.: PCT/EP2007/058491
§ 371 (c)(1),
(2), (4) Date: Mar. 24, 2009

(87) PCT Pub. No.: WO2008/037541
PCT Pub. Date: Apr. 3, 2008

(65) Prior Publication Data
US 2010/0028271 A1 Feb. 4, 2010

(30) Foreign Application Priority Data
Sep. 27, 2006 (DE) .................. 10 2006 045 965

(51) Int. Cl.
| | |
|---|---|
| *A61K 8/81* | (2006.01) |
| *A61K 8/00* | (2006.01) |
| *A61K 9/00* | (2006.01) |
| *A61K 8/18* | (2006.01) |
| *A61K 8/73* | (2006.01) |
| *A61Q 5/06* | (2006.01) |
| *C08K 5/00* | (2006.01) |
| *C08L 39/00* | (2006.01) |
| *C07D 233/36* | (2006.01) |

(52) U.S. Cl. ............. 424/70.1; 424/70.13; 424/70.15; 424/70.16; 424/47; 524/280; 524/282; 524/284; 524/808; 524/809

(58) Field of Classification Search ........ 424/47, 424/70.13, 70.15, 70.16; 524/280, 808
See application file for complete search history.

(56) References Cited

U.S. PATENT DOCUMENTS

| | | | |
|---|---|---|---|
| 3,753,968 | A | 8/1973 | Ward |
| 5,773,595 | A | 6/1998 | Weuthen et al. |
| 6,060,071 | A | 5/2000 | Motitschke et al. |
| 6,235,913 | B1 | 5/2001 | Raths et al. |
| 6,267,973 | B1 | 7/2001 | Motitschke et al. |
| 6,403,112 | B2 | 6/2002 | Motitschke et al. |
| 7,332,466 | B2 | 2/2008 | Schmid et al. |
| 2005/0129650 | A1 | 6/2005 | Marie et al. |
| 2008/0194708 | A1 | 8/2008 | Hossel et al. |

FOREIGN PATENT DOCUMENTS

| | | |
|---|---|---|
| AU | 730455 B2 | 5/2000 |
| AU | 2003280329 A1 | 4/2004 |
| DE | 3139438 A1 | 4/1983 |
| DE | 4413686 C2 | 10/1995 |
| DE | 19736906 A1 | 3/1999 |
| DE | 19738866 A1 | 3/1999 |
| DE | 19756454 C1 | 6/1999 |
| DE | 10240757 A1 | 7/2003 |
| EP | 0671161 A1 | 9/1995 |
| EP | 0998908 A2 | 5/2000 |
| EP | 1598046 A1 | 11/2005 |
| WO | WO-2006/097514 A1 | 9/2006 |

OTHER PUBLICATIONS

"Luviquat Polymer Grades: Quaternized copolymers for hair and skin care" (MEMC 050202e-04/ p. 1 of 32), Nov. 2005, Technical Information, Online http://www.cosmetics.basf.de/pdf/Statements/Technical%20Informations/EN/Cosmetic%20Ingredients/EMM%20050202e_Luviquat%20Polymer.pdf.

*Primary Examiner* — Johann Richter
*Assistant Examiner* — Jane C Oswecki
(74) *Attorney, Agent, or Firm* — David P. LeCroy

(57) ABSTRACT

The invention relates to agents for temporarily shaping keratin fibers, said agents containing: a) at least one film-forming and/or setting amphoteric polymer A and b) at least one copolymer B formed by at least one monomer B1 selected from acrylamide, methacrylamide, N-alkylacrylamide and N-alkylmethacrylamide, at least one monomer B2 selected from N-vinyllactams, at least one monomer B3 selected from quaternized N-vinylimidazoles and the monomer N-vinylimidazole. The invention also relates to the use of the agents for temporarily shaping hair and to an aerosol styling mousse that contains a corresponding agent and at least one propellant.

18 Claims, No Drawings

STYLING AGENTS GIVING AN HIGH DEGREE OF HOLD

RELATED APPLICATIONS

This application is a United States national stage application under 35 U.S.C. §371 of PCT/EP2007/058491, filed Aug. 16, 2007, which claims benefit of German application 102006045965.2, filed Sep. 27, 2006.

The present invention relates to agents for temporary deformation of keratinic fibers, containing a special combination of polymers, the use of these agents for temporarily deformation keratinic fibers and aerosol hair mousses based on these agents.

Keratinic fibers are understood in principle to include all animal hair, e.g. wool, horsehair, angora hair, furs, feathers and products or textiles manufactured therefrom. However, the keratinic fibers are preferably human hair.

An attractive hair style is generally regarded today as an indispensable part of a good outer appearance. Because of current fasten trends, hair styles that are often regarded as chic are those which, on many types of hair, can be created and/or can be maintained for a longer period of time up to several days only by using styling ingredients. Hair treatment agents that serve to permanently or temporarily impart a shape to hair therefore play an important role. Temporary shaping, which should impart a good hold without damaging the healthful appearance of hair, e.g. its sheen, can be achieved through the use of hair spray, hair wax, hair gels, hair mousses, hair dryers, etc.

Corresponding agents for temporary shaping usually contain synthetic polymers as the shaping component. Preparations containing a dissolved or dispersed polymer may be applied to the hair by means of propellant gases or by a pump mechanism. Hair gels and hair waxes in particular, however, are not usually applied directly to hair but instead are distributed in the hair by means of a comb or hands.

The most important property of an agent for temporary deformation of keratinic fibers, hereinafter also referred to as a styling agent, consists of imparting the strongest possible hold to the treated fibers in the shape created. If the keratinic fibers are human hair, one also speaks of a strong styling hold or a high degree of hold of the styling agent. The styling hold is determined essentially by the type and quantity of synthetic polymer used, but there may also be an influence of the other components of the styling agent.

In addition to a high degree of hold, styling agents must also meet a number of other requirements. These may be subdivided roughly into properties on the hair, properties of the respective formulation, e.g. properties of the foam, the gel or the aerosol spray and properties pertaining to the handling of the styling agent, but the properties on the hair are especially important. Moisture resistance, low stickiness and a balanced conditioning effect should be mentioned in particular. In addition, a styling agent should be universally usable for all types of hair.

To do justice to the various requirements, various synthetic polymers have already been developed and are being used in styling agents. These polymers can be subdivided into cationic, anionic, nonionic and amphoteric film-forming and setting polymers. Ideally these polymers form a polymer film when applied to hair, imparting a strong hold to the hairstyle on the one hand but on the other hand also being sufficiently flexible not to break under stress. If the polymer film is too fragile, so-called film plaques develop, i.e. residues which are shed with movement of the hair and give the impression that the user of the respective styling agent has dandruff.

To develop styling agents having all the desired properties in combination still presents problems. This is true in particular of styling agents that should have an especially strong hold.

The object of the present invention was therefore to make available an agent for temporary deformation of keratinic fibers, such that it will be characterized by a very high degree of hold without any loss of flexibility or good moisture resistance.

It has now surprisingly been found that this can be achieved through a combination of special polymers.

A first subject matter of the present invention is therefore an agent for temporary deformation of keratinic fibers, containing in a cosmetically acceptable carrier
    a) at least one film-forming and/or setting amphoteric polymer A and
    b) at least one polymer B made up from:
        at least one monomer B1 selected from acrylique acid amide, methacrylique acid amide, N-alkylacrylique acid amide and N-alkyl-methacrylique acid amide,
        at least one monomer B2 selected from N-vinyllactams,
        at least one monomer B3 selected from quaternized N-vinylimidazoles, and
        the monomer N-vinylimidazole.

Film-forming and/or setting amphoteric polymers A are known. The same is also true of copolymers B and their use as film-forming and/or setting polymers. The copolymers B are characterized in particular by a very high degree of hold. It has now surprisingly been found that when using a combination of these polymers, a synergistic increase in the degree of hold is achieved, in particular in high atmospheric humidity.

As the first obligatory component, the inventive agents for temporary deformation of keratinic fibers contain at least one film-forming and/or setting amphoteric polymer A.

The film-forming and/or setting amphoteric polymer A is preferably selected from the group of methacryloyl betaine/alkyl methacrylate copolymers, copolymers of monomers with carboxyl and/or sulfonic groups, in particular acrylic acid, methacrylic acid, itaconic acid and monomers with amino groups, in particular monoalkylaminoalkyl acrylates, dialkylaminoalkyl acrylates, monoalkylaminoalkyl methacrylates, dialkylaminoalkyl methacrylates, monoalkylaminoalkyl acrylique acid amides, dialkylaminoalkyl acrylique acid amides, monoalkylaminoalkyl methacrylique acid amides, dialkylaminoalkyl methacrylique acid amides and copolymers of N-octylacrylique acid amide, methyl methacrylate, hydroxypropyl methacrylate; N-tert-butylaminoethyl methacrylate and acrylic acid.

The inventive agent particularly preferably contains as the film-forming and/or setting amphoteric polymer A an N-octylacrylamide/acrylic acid/tert-butylaminoethyl methacrylate copolymer, in particular preferably the copolymer distributed by the company National Starch under the brand name Amphomer® (INCI designation: octylacrylique acid amide/acrylates/butylaminoethyl methacrylate copolymer).

The film-forming and/or setting amphoteric polymer A is preferably contained in an amount of 0.01 to 20 wt %, preferably 0.1 to 15 wt %, particularly preferably 1.0 to 10 wt %, based on the total hair-setting agent. Multiple film-forming and/or setting amphoteric polymers may of course also be included, but the total amount of film-forming and/or setting amphoteric polymers is preferably max. 20 wt %.

As the second obligatory component, the inventive agents for temporarily deformation keratinic fibers contain at least one copolymer B.

Preferred for use here is a copolymer B made up from:
    at least one monomer B1 selected from acrylique acid amide, methacrylique acid amide, N—$C_1$-$C_{10}$-alkylacrylique acid amide and N—$C_1$-$C_{10}$-alkylmethacrylique acid amide, at least one monomer B2 selected from N-vinyllactams,
at least one monomer B3 selected from quaternized N-vinylimidazoles, and
the monomer N-vinylimidazole.

Copolymers B which are made up from the aforementioned monomers are understood in the sense of the present invention to be only those copolymers which contain, in addition to polymer units resulting from the incorporation of the aforementioned monomers of B1, B2, B3 and N-vinylimidazole into the copolymer, max. 5 wt %, preferably max. 1 wt % polymer units attributed to the incorporation of other monomers. The copolymers B are preferably synthesized exclusively from polymer units which result from the incorporation of the aforementioned monomers B1, B2, B3 and N-vinylimidazole into the copolymer.

Preferred monomers B1 are acrylique acid amide and methacrylique acid amide, methacrylique acid amide being especially preferred.

Preferred monomers B2 are N-vinylcaprolactam and N-vinylpyrrolidone, N-vinylpyrrolidone being especially preferred.

Preferred monomers B3 are salts of 3-alkyl-1-vinylimidazolium, in particular 3-($C_1$-$C_{10}$-alkyl)-1-vinylimidazolium with physiologically acceptable anions. Suitable physiologically acceptable anions include in particular halides such as chloride, bromide and iodide, bicarbonate, bisulfate, monoalkyl sulfate, in particular monomethyl sulfate and dihydrogen phosphate. Preferred physiologically tolerable anions include chloride and monomethyl sulfate.

Monomer B3 is particularly preferably 3-methyl-1-vinylimidazolium methyl sulfate.

An especially preferred copolymer B is made up from:
at least one monomer B1 selected from acrylique acid amide and methacrylique acid amide,
at least one monomer B2 selected from N-vinylcaprolactam and N-vinylpyrrolidone,
3-methyl-1-vinylimidazolium methyl sulfate and
N-vinylimidazole.

The copolymers B can be synthesized from the aforementioned monomers by means of the known polymerization methods.

Most especially preferred copolymers B are the copolymers that are known as polyquaternium-68 according to INCI nomenclature and are synthesized from vinylpyrrolidone, methacrylique acid amide, vinylimidazole and 3-methyl-1-vinylimidazolium methyl sulfate. These are commercially available under the brand name Luviquat® Supreme.

The inventive agents preferably contain the copolymer B in an amount of 0.01 to 20 wt %, particularly preferably 0.05 to 10 wt %, most particularly preferably 0.1 to 5 wt %, based on the total hair-setting agent.

The inventive agents may of course also contain several copolymers B, but the total amount of copolymer B is preferably max. 20 wt %.

To achieve the desired properties of the inventive agent, in particular the very strong hold in combination with an excellent moisture resistance, the agents must contain both a film-forming and/or setting amphoteric polymer A and copolymer B. It has been found that an optimal profile of properties is obtained when the agent contains the film-forming and/or setting amphoteric polymer A and copolymer B in a weight ratio of 1:20 to 20:1, preferably 1:10 to 10:1, particularly preferably from 1:5 to 5:1, most particularly preferably 1:3 to 3:1. In a special embodiment, the agent contains the film-forming and/or setting amphoteric polymer A and the copolymer B in a weight ratio of 1:1 to 3:1.

In addition to film-forming and/or setting amphoteric polymers A and copolymer B, the agents may also contain all other known film-forming and/or setting polymers. These film-forming and/or setting polymers may be either permanently or temporarily cationic, anionic or nonionic.

Since polymers are often multifunctional, their functions cannot always be clearly and unambiguously demarcated from one other. This is true in particular of film-forming and setting polymers. However, it should be pointed out explicitly here that within the scope of the present invention, both film-forming and setting polymers are essential. However, since the two properties are not completely independent of one another, the term "setting polymers" is also always understood to include "film-forming polymers" and vice-versa.

The preferred properties of the film-forming polymers include the formation of a film. Film-forming polymers are understood to be polymers which, when dry, leave a continuous film on the skin, hair or nails. Such film-forming agents may be used in a wide variety of cosmetic products, e.g. face masks, makeup, hair-setting lotions, hair sprays, hair gels, hair waxes, hair treatments, shampoos or nail polish. Polymers having a sufficient solubility in alcohol or water/alcohol mixtures to be present in completely dissolved form in the inventive agents are preferred in particular. The film-forming polymers may be of synthetic or natural origin.

Film-forming polymers are also understood to include polymers which are capable of depositing a transparent polymer film on the hair when used in 0.01 to 20 wt % aqueous, alcoholic or aqueous-alcoholic solution.

Suitable additional film-forming, hair-setting polymers include, for example, homopolymers or copolymers synthesized from at least one of the following monomers: vinylpyrrolidone, vinyl caprolactam, vinyl esters, e.g. vinyl acetate, vinyl alcohol, acrylique acid amide, methacrylique acid amide, alkylacrylique acid amide and dialkylacrylique acid amide, alkylmethacrylique acid amide and dialkylmethacrylique acid amide, alkyl acrylate, alkyl methacrylate, propylene glycol or ethylene glycol, where the alkyl groups of these monomers are preferably $C_1$ to $C_7$ alkyl groups, particularly preferably $C_1$ to $C_3$ alkyl groups.

Examples that can be mentioned include the homopolymers of vinyl caprolactam, vinylpyrrolidone or N-vinylformamide. Other suitable synthetic film-forming, hair-setting polymers include, for example, copolymers of vinylpyrrolidone and vinyl acetate, terpolymers of vinylpyrrolidone, vinyl acetate and vinyl propionate, polyacrylique acid amides, which are distributed, for example, under the brand names Akypomine® P 191 by the company CHEM-Y, Emmerich, or Sepigel® 305 by the company Seppic; polyvinyl alcohols, which are distributed under the brand names Elvanol® by DuPont or Vinol 523/540 by the company Air Products as well as polyethylene glycol/polypropylene glycol copolymers, which are distributed, for example, under the brand names Ucon® by Union Carbide.

Suitable natural film-forming polymers include, for example, cellulose derivatives, e.g. hydroxypropylcellulose with a molecular weight of 30,000 to 50,000 g/mol, which is distributed, for example, under the brand name Nisso Si® by the company Lehmann & Voss, Hamburg.

Setting polymers contribute to the hold and/or to the creation of hair volume and to the body of the overall hair style. These so-called setting polymers are at the same time also film-forming polymers and therefore are typical substances in general for shaping hair treatment agents such as hair-setting agents, hair mousses, hair waxes, hair sprays. The formation of a film may take place in spots or may join only a few fibers together.

Substances that also impart hydrophobic properties to hair are preferred here because they reduce the tendency of hair to absorb moisture, i.e. water. This therefore prevents strands of hair from hanging down limply and thus ensures a long-lasting set and hold. The so-called curl retention test is often used as a test method for this. These polymer substances may also be successfully incorporated into leave-on and rinse-off hair treatments or shampoos. Polymers are often multifunctional, i.e. have multiple desired effects in terms of applications technology, so there are numerous polymers in several groups divided according to the mechanism of action, e.g. in the CTFA Handbook.

If the inventive agents contain additional film-forming and/or setting polymers, they are preferably used in an amount of 0.01 to 20 wt %, particularly 0.1 to 15 wt %, based on the total hair-setting agent. Multiple film-forming and/or setting polymers may of course be included, but the total amount of other film-forming and/or setting polymers is preferably max. 20 wt %.

In a preferred embodiment, the inventive agents contain exclusively film-forming and/or setting amphoteric polymers A and copolymers B as the film-forming and/or setting polymers.

The inventive agents contain the copolymers in a cosmetically acceptable carrier.

Preferred cosmetically acceptable carriers are aqueous, alcoholic or aqueous-alcoholic media, preferably with at least 10 wt % water, based on the total agent. The low alcohols with one to four carbon atoms such as ethanol and isopropanol, which are generally used for cosmetic purposes in particular, may also be present as the alcohols.

As additional co-solvents, organic solvents or a mixture of solvents with a boiling point lower than 400° C. may be contained in an amount of 0.1 to 15 wt %, preferably from 1 to 10 wt %, based on the total agent. Branched or unbranched hydrocarbons such as pentane, hexane, isopentane and cyclic hydrocarbons such as cyclopentane and cyclohexane are especially suitable as additional co-solvents. Other especially preferred solvents water-soluble include glycerol, ethylene glycol and propylene glycol in an amount of up to 30 wt %, based on the total agent.

The addition of glycerol and/or propylene glycol in particular increases the flexibility of the polymer film formed when using the inventive agent. Thus when a flexible hold is desired, the inventive agents preferably contain 0.01 to 30 wt % glycerol and/or propylene glycol, based on the total agent.

The agents preferably have a pH from 2 to 11. The pH range is particularly preferably between 2 and 8. Unless otherwise indicated, statements about pH in the sense of this document are based on the pH at 25° C.

The inventive agents may also contain the additives and auxiliary substances that are usually added to traditional styling agents.

Suitable additives and auxiliary substances include in particular care substances.

Care substances that may be used include, for example, a silicone oil and/or a silicone gum. In an especially preferred embodiment of the invention, the agents contain at least one silicone oil and/or one silicone gum.

Silicone oils or silicone gums suitable according to the invention include in particular dialkylsiloxanes and alkylarylsiloxanes, for example, dimethylpolysiloxane and methylphenylpolysiloxane as well as their alkoxylated, quaternized or anionic derivatives. Cyclic and linear polydialkylsiloxanes, their alkoxylated and/or aminated derivatives, dihydroxypolydimethylsiloxanes and polyphenylalkylsiloxanes are preferred.

Silicone oils produce a wide variety of effects. For example, they simultaneously influence the dry and wet combability, the feel of the dry and wet hair as well as its sheen. The term "silicone oils" is understood by those skilled in the art to include several structures of organosilicon compounds. These are first understood to include the dimethiconols (S1), which may be linear as well as branched as well as cyclic or cyclic and branched. Linear dimethiconols may be represented by the following structural formula (S1-I):

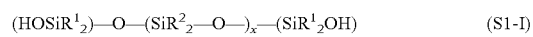

(S1-I)

Branched dimethiconols may be represented by the structural formula (S1-II):

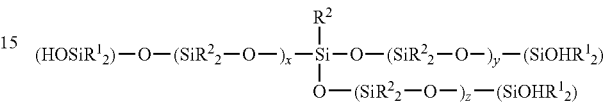

(S1-II)

The radicals $R^1$ and $R^2$ independently of one another each stand for hydrogen, a methyl radical, a $C_2$ to $C_{30}$ linear, saturated or unsaturated hydrocarbon radical, a phenyl radical and/or an aryl radical. Nonrestrictive examples of the radicals represented by $R^1$ and $R^2$ include alkyl radicals such as methyl, ethyl, propyl, isopropyl, butyl, isobutyl, pentyl, isopentyl, neopentyl, amyl, isoamyl, hexyl, isohexyl and the like; alkenyl radicals such as vinyl, halovinyl, alkylvinyl, allyl, haloallyl, alkylallyl; cycloalkyl radicals such as cyclobutyl, cyclopentyl, cyclohexyl and the like; phenyl radicals, benzyl radicals, halohydrocarbon radicals such as 3-chloropropyl, 4-bromobutyl, 3,3,3-trifluoropropyl, chlorocyclohexyl, bromophenyl, chlorophenyl and the like as well as radicals containing sulfur, such as mercaptoethyl, mercaptopropyl, mercaptohexyl, mercaptophenyl and the like; $R^1$ and $R^2$ are preferably an alkyl radical containing from one to approximately six carbon atoms, but $R^1$ and $R^2$ are in particular preferably methyl. The numbers x, y and z are integers and each independently of the others amounts to 0 to 50,000. The molecular weights of the dimethiconols are between 1000 D and 10,000,000 D. The viscosities are between 100 and 10,000,000 cPs, measured at 25° C. with the help of a glass capillary viscometer according to the Dow Corning Corporate Test Method CTM 0004 of Jul. 20, 1970. Preferred viscosities are between 1000 and 5,000,000 cPs, and most especially preferred viscosities are between 10,000 and 3,000,000 cPs. The most preferred range is between 50,000 and 2,000,000 cPs.

The following commercial products are mentioned as examples of such products. Botanisil NU-150M (Botanigenics), Dow Corning 1-1254 Fluid, Dow Corning 2-9023 Fluid, Dow Corning 2-9026 Fluid, Ultrapure Dimethiconol (Ultra Chemical), Unisil SF-R (Universal Preserve), X-21-5619 (Shin-Etsu Chemical Co.), Abil OSW 5 (Degussa Care Specialties), ACC DL-9430 Emulsion (Taylor Chemical Company), AEC dimethiconol and sodium dodecylbenzenesulfonate (A & E Connock (Perfumery & Cosmetics) Ltd.), B C Dimethiconol Emulsion 95 (Basildon Chemical Company, Ltd.), Cosmetic Fluid 1401, Cosmetic Fluid 1403, Cosmetic Fluid 1501, Cosmetic Fluid 1401DC (all the aforementioned are from Chemisil Silicones, Inc.), Dow Corning 1401 Fluid, Dow Corning 1403 Fluid, Dow Corning 1501 Fluid, Dow Corning 1784 HVF emulsion, Dow Corning 9546 Silicone Elastomer Blend (all the aforementioned are from Dow Corning Corporation), Dub Gel SI 1400 (Stearinerie Dubois Fils), HVM 4852 emulsion (Crompton Corporation), Jeesilc 6056 (Jeen International Corporation), Lubrasil, Lubrasil DS (both from Guardian Laboratories), Nonychosine E, Nonychosine V (both Exsymol), SanSurf Petrolatum-25, Satin Finish (both from Collaborative Laboratories, Inc.), Silatex-D30 (Cosmetic Ingredient Resources), Silsoft 148, Silsoft E-50, Silsoft E-623 (all the aforementioned are from Crompton Corporation), SM555, SM2725, SM2765, SM2785 (all the aforementioned are from GE Silicones), Taylor T-Sil CD-1, Taylor TME-4050E (all from Taylor Chemical Company), THV 148 (Crompton Corporation), Tixogel CYD-1429 (Süd-Chemie Performance Additives), Wacker-Belsil CM 1000, Wacker-Belsil CM 3092, Wacker-Belsil CM 5040, Wacker-Belsil DM 3096, Wacker-Belsil DM 3112 VP, Wacker-Belsil DM 8005 VP, Wacker-Belsil DM 60081 VP (all the aforementioned are from Wacker-Chemie GmbH).

Dimethicones (S2) are the second group of silicones that may be included according to the invention. They may be linear as well as branched and cyclic or cyclic and branched. Linear dimethicones may be represented by the following structural formula (S2-I):

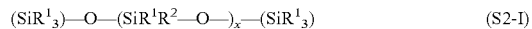  (S2-I)

Branched dimethicones may be represented by the structural formula (S2-II):

(S2-II)

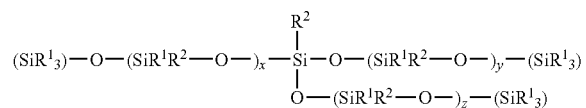

The $R^1$ and $R^2$ radicals, independently of one another, each stand for hydrogen, a methyl radical, a $C_2$ to $C_{30}$ linear, saturated or unsaturated hydrocarbon radical, a phenyl radical and/or an aryl radical. Nonrestrictive examples of the radicals represented by $R^1$ and $R^2$ include alkyl radicals such as methyl, ethyl, propyl, isopropyl, butyl, isobutyl, pentyl, isopentyl, neopentyl, amyl, isoamyl, hexyl, isohexyl and the like; alkenyl radicals such as vinyl, halovinyl, alkylvinyl, allyl, haloallyl, alkylallyl; cycloalkyl radicals such as cyclobutyl, cyclopentyl, cyclohexyl and the like; phenyl radicals, benzyl radicals, halohydrocarbon radicals such as 3-chloropropyl, 4-bromobutyl, 3,3,3-trifluoropropyl, chlorocyclohexyl, bromophenyl, chlorophenyl and the like as well as radicals containing sulfur such as mercaptoethyl, mercaptopropyl, mercaptohexyl, mercaptophenyl and the like; $R^1$ and $R^2$ are preferably an alkyl radical containing from one to approximately six carbon atoms, but $R^1$ and $R^2$ are in particular preferably methyl. The numbers x, y and z are integers and each independently of the others amounts to 0 to 50,000. The molecular weights of the dimethiconols are between 1000 D and 10,000,000 D. The viscosities are between 100 and 10,000,000 cPs, measured at 25° C. with the help of a glass capillary viscometer according to the Dow Corning Corporate Test Method CTM 0004 of Jul. 20, 1970. Preferred viscosities are between 1000 and 5,000,000 cPs, most especially preferred viscosities are between 10,000 and 3,000,000 cPs. The viscosity is most particularly preferably in the range between 50,000 and 2,000,000 cPs.

Dimethicone copolyols (S3) are another group of silicones that are suitable. Dimethicone copolymers can be synthesized according to the following structural formulas:

$(SiR^1{}_3)$—O—$(SiR^2{}_2$—O—$)_x(SiR^2PE\text{-}O$—$)_y$—$(SiR^1{}_3)$  (S3-I), PE-$(SiR^1{}_2)$—O—$(SiR^2{}_2$—O—$)_x$—$(SiR^1{}_2)$-PE  (S3-II)

Branched dimethicone copolyols can be synthesized according to the structural formula (S3-III):

(S3-III)

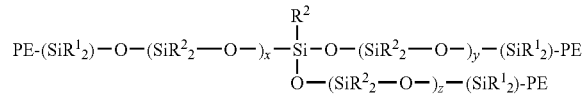

or by the structural formula (S3-IV):

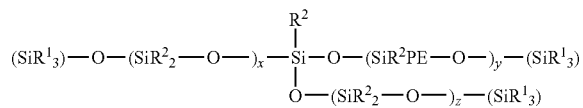

The $R^1$ and $R^2$ radicals, independently of one another, each stand for hydrogen, a methyl radical, a $C_2$ to $C_{30}$ linear, saturated or unsaturated hydrocarbon radical, a phenyl radical and/or an aryl radical. Nonrestrictive examples of the radicals represented by $R^1$ and $R^2$ include alkyl radicals such as methyl, ethyl, propyl, isopropyl, butyl, isobutyl, pentyl, isopentyl, neopentyl, amyl, isoamyl, hexyl, isohexyl and the like; alkenyl radicals such as vinyl, halovinyl, alkylvinyl, allyl, haloallyl, alkylallyl; cycloalkyl radicals such as cyclobutyl, cyclopentyl, cyclohexyl and the like; phenyl radicals, benzyl radicals, halohydrocarbon radicals such as 3-chloropropyl, 4-bromobutyl, 3,3,3-trifluoropropyl, chlorocyclohexyl, bromophenyl, chlorophenyl and the like as well as radicals containing sulfur, such as mercaptoethyl, mercaptopropyl, mercaptohexyl, mercaptophenyl and the like; $R^1$ and $R^2$ are preferably an alkyl radical containing from one to approximately six carbon atoms, but $R^1$ and $R^2$ are in particular preferably methyl. PE stands for a polyoxyalkylene radical. Preferred polyoxyalkylene radicals are derived from ethylene oxide, propylene oxide and glycerol. The numbers x, y and z are integers and each independently of the others amounts to 0 to 50,000. The molecular weights of the dimethiconols are between 1000 D and 10,000,000 D. The viscosities are between 100 and 10,000,000 cPs measured at 25° C. with the help of a glass capillary viscometer according to the Dow Corning Corporate Test Method CTM 0004 of Jul. 20, 1970. Preferred viscosities are between 1000 and 5,000,000 cPs, most especially preferred viscosities are between 10,000 and 3,000,000 cPs. The viscosity is most particularly preferably in the range between 50,000 and 2,000,000 cPs.

Corresponding dimethicone copolyols are commercially available and are distributed by the company Dow Corning under the brand name Dow Corning® 5330 Fluid, for example.

The inventive teaching of course also includes the fact that the dimethiconols, dimethicones and/or dimethicone copolymers may already be in the form of an emulsion. The corresponding emulsion of the dimethiconols, dimethicones and/or dimethicone copolyols can be produced after preparation of the corresponding dimethiconols, dimethicones and/or dimethicone copolyols using the conventional methods of emulsification with which those skilled in the art are familiar. To do so, cationic, anionic, nonionic or zwitterionic surfactants and emulsifiers may be used as auxiliary substances to produce the corresponding emulsions. The emulsions of the dimethiconols, dimethicones and/or dimethicone copolyols may of course also be prepared directly by an emulsion polymerization method. Those skilled in the art are well aware of such methods.

If the dimethiconols, dimethicones and/or dimethicone copolyols are used as an emulsion, then the droplet size of the emulsified particles according to the invention amounts to 0.01 to 10,000 μm, preferably 0.01 to 100 μm, particularly preferably 0.01 to 20 μm and most particularly preferably 0.01 to 10 μm. The particle size is determined according to the light scatter method.

If branched dimethiconols, dimethicones and/or dimethicone copolyols are used, then this is to be understood as meaning that the branching is greater than a random branching which occurs due to impurities in the respective monomers. In the sense of the present invention, branched dimethiconols, dimethicones and/or dimethicone copolyols are to be understood as meaning that the degree of branching is greater than 0.01%. A degree of branching greater than 0.01% and most particularly preferably greater than 0.5% is preferred. The degree of branching is determined from the ratio of the unbranched monomers to the branched monomers, i.e. the amount of trifunctional and tetrafunctional siloxanes. According to the invention, both low-branched and high-branched dimethiconols, dimethicones and/or dimethicone copolyols are most especially preferred.

Suitable silicones also include aminofunctional silicones (S4), in particular the silicones combined under the INCI designation amodimethicones. These are understood to include silicones having at least one optionally substituted amino group.

Such silicones can be described, for example, by the formula (S4-I)

$$M(R_aQ_bSiO_{(4-a-b)/2})_x(R_cSiO_{(4-c)/2})_yM \qquad (S4\text{-}I)$$

where R in the above formula is a hydrocarbon or a hydrocarbon radical with one to approximately six carbon atoms, Q is a polar radical of the general formula $R^1Z$, where $R^1$ denotes a divalent bonding group, which is bonded to hydrogen and to the radical Z, is composed of carbon and hydrogen atoms, carbon, hydrogen and oxygen atoms or carbon, hydrogen and nitrogen atoms, and Z is an organic aminofunctional radical having at least one aminofunctional group; "a" assumes values in the range from approximately 0 to approximately 2, "b" assumes values in the range from approximately 1 to approximately 3; "a" and "b" are less than or equal to 3, and "c" denotes a number in the range from approximately 1 to approximately 3, and x denotes a number in the range from 1 to approximately 2000, preferably from approximately 3 to approximately 50 and most preferably from approximately 3 to approximately 25, and y is a number in the range from approximately 20 to approximately 10,000, preferably from approximately 125 to approximately 10,000 and most preferably from approximately 150 to approximately 1000, and M is a suitable silicone end group, such as that known in the state of the art, preferably trimethylsiloxy. Nonrestrictive examples of the radicals represented by R include alkyl radicals such as methyl, ethyl, propyl, isopropyl, butyl, isobutyl, amyl, isoamyl, hexyl, isohexyl and the like; alkenyl radicals such as vinyl, halovinyl, alkylvinyl, allyl, haloallyl, alkylallyl; cycloalkyl radicals such as cyclobutyl, cyclopentyl, cyclohexyl and the like; phenyl radicals, benzyl radicals, halohydrocarbon radicals such as 3-chloropropyl, 4-bromobutyl, 3,3,3-trifluoropropyl, chlorocyclohexyl, bromophenyl, chlorophenyl and the like as well as radicals containing sulfur such as mercaptoethyl, mercaptopropyl, mercaptohexyl, mercaptophenyl and the like; R is preferably an alkyl radical containing one to approximately six carbon atoms, and R is most preferably methyl. Examples of $R^1$ include methylene, ethylene, propylene, hexamethylene, decamethylene, $CH_2CH(CH_3)CH_2$, phenylene, naphthylene, $CH_2CH_2SCH_2CH_2$, $CH_2CH_2OCH_2$, $OCH_2CH_2$, $OCH_2CH_2CH_2$, $CH_2CH(CH_3)C(O)OCH_2$, $(CH_2)_3C(O)OCH_2CH_2$, $C_6H_4C_6H_4$, $C_6H_4CH_2C_6H_4$ and $(CH_2)_3C(O)SCH_2CH_2$.

Z is an organic aminofunctional radical containing at least one functional amino group. A possible formula for Z is $NH(CH_2)_nNH_2$, in which z stands for an integer from 1 to 50. Another possible formula for Z is $NH(CH_2)_zNH(CH_2)_{zz}$ in which both z and zz, independently of one another, stand for an integer from 1 to 50, where this structure includes diamino ring structures such as piperazinyl. Z is particularly preferably an $NHCH_2CH_2NH_2$ radical. Another possible formula for Z is $N(CH_2)_zNX^1X^2$ or $NX^1X^2$, in which $X^1$ and $X^2$, independently of one another, are each selected from hydrogen and a hydrocarbon radical with one to approximately six carbon atoms.

Most particularly preferably, Q stands for a polar aminofunctional radical of the formula $CH_2CH_2CH_2NHCH_2CH_2NH_2$.

The molar ratio of $R_aQ_bSiO_{(4-a-b)/2}$ units to the $R_cSiO_{(4-c)/2}$ units is in the range from approximately 1:2 to 1:65, preferably from approximately 1:5 to approximately 1:65 and particularly preferably from approximately 1:15 to approximately 1:20. If one or more silicones of the above formula are used, then the various variable substituents in the above formula may be different in the various silicone components present in the silicone mixture.

Preferred aminofunctional silicones correspond to the formula (S4-II)

$$R'_aG_{3-a}\text{-}Si(OSiG_2)_n\text{-}(OSiG_bR'_{2-b})_m\text{-}O\text{-}SiG_{3-a}\text{-}R'_a \qquad (S4\text{-}II),$$

in which

G is H, a phenyl group, OH, $O\text{-}CH_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$;

a stands for a number between 0 and 3, in particular 0;

b stands for a number between 0 and 1, in particular 1;

m and n are numbers, the sum of which (m+n) is between 1 and 2000, preferably between 50 and 150, where n preferably assumes values from 0 to 1999 and in particular from 49 to 149, and m preferably assumes values from 1 to 2000, in particular from 1 to 10;

R' is a monovalent radical selected from:
—N(R")—CH$_2$—CH$_2$—N(R")$_2$
—N(R")$_2$
—N$^+$(R')$_3$A$^-$
—N$^+$H(R")$_2$A$^-$
—N$^+$H$_2$(R")A$^-$
—N(R")—CH$_2$—CH$_2$—N$^+$R"H$_2$A$^-$, where each R" stands for the same or different radicals from the group of H, phenyl, benzyl, $C_{1-20}$ alkyl radicals, preferably $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$ and A$^-$ represents an anion that is preferably selected from chloride, bromide, iodide or methosulfate.

Especially preferred aminofunctional silicones correspond to the formula (S4-III)

$$(CH_3)_3Si\text{---}[O\text{---}Si(CH_3)_2]_n[OSi(CH_3)]_m\text{---}OSi(CH_3)_3$$
$$|$$
$$CH_2CH(CH_3)CH_2NH(CH_2)_2NH_2,$$

(S4-III)

in which m and n are numbers, the sum of which (m+n) is between 1 and 2000, preferably between 50 and 150, where n preferably assumes values from 0 to 1999 and in particular from 49 to 149, and m preferably assumes values of 1 to 2000, in particular 1 to 10.

According to the INCI declaration, these silicones are designated as trimethylsilylamodimethicone.

In addition, aminofunctional silicones of the formula (S4-IV) are especially preferred $$R\text{---}[Si(CH_3)_2\text{---}O]_{n1}[Si(R)\text{---}O]_m\text{---}[Si(CH_3)_2]_{n2}\text{---}R,$$
$$|$$
$$(CH_2)_3NH(CH_2)_2NH_2$$

(S4-IV)

in which R stands for OH, O—CH$_3$ or a CH$_3$ group and m, n1 and n2 are numbers, the sum of which (m+n1+n2) is between 1 and 2000, preferably between 50 and 150, where the sum (n1+n2) preferably assumes values from 0 to 1999 and in particular from 49 to 149, and m preferably assumes values from 1 to 2000 in particular from 1 to 10.

These silicones are designated as amodimethicone according to the INCI declaration and are available, e.g. in the form of an emulsion as a commercial product from Dow Corning® 949 in mixture with a cationic surfactant and a nonionic surfactant.

Such aminofunctional silicones having an amine number above 0.25 meq/g, preferably above 0.3 meq/g and in particular preferably above 0.4 meq/g are preferably used. The amine number stands for milliequivalents of amine per gram of aminofunctional silicone. This can be determined by titration and is also given in the unit mg KOH/g.

Additional suitable silicones include, for example:
oligomeric polydimethylcyclosiloxanes (INCI designation cyclomethicone), in particular the tetrameric and pentameric compounds distributed as the commercial products DC 245 Fluid, DC 344 and/or DC 345 by Dow Corning,
hexamethyldisiloxane (INCE designation: hexamethyldisiloxane), e.g. the product distributed under the name Abil® K 520,
polyphenylmethylsiloxanes (INCI designation: phenyl trimethicone), e.g. the commercial product DC 556 Cosmetic Grade Fluid from Dow Corning,
esters and partial esters of silicone-glycol copolymers such as those distributed by the company Fanning under the brand name Fancorsil® LIM (INCI designation: dimethicone copolyol meadow-foamate),
anionic silicone oils such as the product Dow Corning® 1784, for example.

According to a preferred embodiment, the inventive agent contains at least two different silicone derivatives, in particular preferably a combination of a volatile silicone and a nonvolatile silicone. Volatile in the sense of the invention are silicones having a volatility equal to or greater than the volatility of the cyclic pentameric dimethylsiloxane. Such combinations are also available as commercial products (e.g. Dow Corning® 1401, Dow Corning® 1403 and Dow Corning® 1501, each as mixtures of a cyclomethicone and a dimethiconol).

Preferred mixtures of various silicones include, for example, dimethicone and dimethiconols, linear dimethicones and cyclic dimethiconols. A most especially preferred mixture of silicones consists of at least one cyclic dimethiconol and/or dimethicone, at least one additional noncyclic dimethicone and/or dimethiconol and at least one aminofunctional silicone.

If different silicones are used as a mixture, then the mixing ratio is largely variable. However, all silicones used for the mixture are preferably used in a ratio of 5:1 to 1:5 in the case of binary mixture. A ratio of 3:1 to 1:3 is especially preferred. Most especially preferred mixtures contain all the silicones contained in the mixture largely in a ratio of approximately 1:1, each based on the amounts used in wt %.

The agents preferably contain the silicone in amounts of 1-25 wt %, particularly preferably 5-20 wt % and in particular preferably 7-15 wt %, based on the total agent.

Although the inventive agent preferably contains a silicone derivative as the care substance, it is also possible for the agent to contain at least one care substance of another class of compounds in addition to a silicone component.

As a care substance of another class of compounds, the agent may contain, for example, at least one protein hydrolyzate and/or one of its derivatives.

Protein hydrolyzates are product mixtures obtained by acidic, basic or enzymatic catalytic degradation of proteins. The term protein hydrolyzates is also understood according to the invention to refer to individual amino acids and their derivatives as well as mixtures of different amino acids. In addition, the term protein hydrolyzates is also understood to include polymers composed of amino acids and amino acid derivatives according to the invention. The protein hydrolyzates include, for example, polyalanine, polyasparagine, polyserine, etc. Other examples of compounds usable according to the invention include L-alanyl-L-proline, polyglycine, glycyl-L-glutamine or D/L-methionine-5-methylsulfonium chloride. β-Amino acids and their derivatives such as β-alanine, anthranilic acid or hippuric acid may of course also be used according to the invention. The molecular weight of the protein hydrolyzates usable according to the invention is between 75 daltons, the molecular weight of glycine, and 200,000 daltons; the molecular weight preferably amounts to 75 to 50,000 daltons and most particularly preferably 75 to 20,000 daltons.

Protein hydrolyzates of both plant and animal origin or marine or synthetic origin may be used according to the invention.

Animal protein hydrolyzates include, for example, elastin, collagen, keratin, silk and milk protein hydrolyzates, which may also be in the form of salts. Such products are distributed, for example, under the brand names Dehylan® (Cognis), Promois® (Interorgana), Collapuron® (Cognis), Nutrilan® (Cognis), Gelita-Sol® (Deutsche Gelatine Fabriken Stoess & Co.), Lexein® (Inolex), sericin (Pentapharm) and Kerasol® (Croda).

The use of silk protein hydrolyzates is especially interesting. The term silk is understood to refer to the fibers of the cocoon of the mulberry silkworm (*Bombyx mori* L.). The raw silk fiber consist of a double fiber fibroin. As a cementing substance, sericin holds this double fiber together. Silk consists of 70-80 wt % fibroin, 19-28 wt % sericin, 0.5-1 wt % fat and 0.5-1 wt % pigments and mineral constituents.

The essential ingredients of sericin are hydroxyamino acids, which account for approximately 46 wt %. Sericin consists of a group of five to six proteins. The essential amino acids of sericin are serine (37 wt % Ser), aspartate (27 wt % Asp), glycine (17 wt % Gly), alanine (Ala), leucine (Leu) and tyrosine (Tyr).

The water-insoluble fibroin is considered to be a scleroprotein with a long-chain molecular structure. The main components of fibroin are glycine (44 wt %), alanine (26 wt %) and tyrosine (13 wt %). Another important structural feature of fibroin is the hexapeptide sequence Ser-Gly-Ala-Gly-Ala-Gly.

It is technically possible in a simple manner to separate the two silk proteins from one another. It is thus not surprising that both sericin and fibroin are known separately as raw materials for use in cosmetic products. In addition, protein hydrolyzates and derivatives based on the respective individual silk proteins are raw materials known for use in cosmetic agents. For example, sericin as such has been distributed by the company Pentapharm Ltd. as a commercial product under the brand name Sericin Code 303-02. Fibroin, however, is offered far less often on the market as a protein hydrolyzate with different molecular weights. These hydrolyzates are distributed as "silk hydrolyzates" in particular. For example, hydrolyzed fibroin with average molecular weights between 350 and 1000 is distributed under the brand name Promois® Silk.

The positive properties of the silk protein derivatives from sericin and fibroin are each known separately in the literature.

For example, the retail brochure from the company Pentapharm describes the cosmetic effects of sericin on the skin as relieving irritation, hydrating and forming a film. The effect of a fibroin derivative is described as a hair care and hair finish effect in DE 31 39 438 A1, for example. According to DE 102 40 757 A1, a synergistic increase in the positive effects of silk proteins and their derivatives can be achieved by simultaneous use of sericin and fibroin and/or their derivatives and/or hydrolyzates.

An active ingredient complex (A) consisting of the active ingredient (A1) selected from sericin, sericin hydrolyzates and/or derivative thereof as well as mixtures thereof and an active ingredient (A2) selected from fibroin and/or fibroin hydrolyzates and/or their derivatives and/or mixtures thereof is therefore preferably used as the silk protein hydrolyzate in the inventive agent.

The active ingredient complex (A) significantly improves the essential internal and external structural features described above as well as the strength and elasticity of human hair in a synergistic manner.

The following may be used as active ingredients (A1) in the active ingredient complex (A):
native sericin,
hydrolyzed and/or further derivatized sericin such as commercial products with the INCI designations sericin, hydrolyzed sericin or hydrolyzed silk,
a mixture of the amino acids serine, aspartate and glycine and/or their methyl, propyl, isopropyl, butyl, isobutyl esters, their salts such as hydrochlorides, sulfates, acetates, citrates, tartrates, whereby serine and/or its derivatives are present in this mixture in amounts of 20 to 60 wt %, aspartate and/or its derivatives are present in amounts of 10 to 40 wt %, and glycine and/or its derivatives are present in amounts of 5 to 30 wt %, with the provision that the amounts of these amino acids and/or their derivatives preferably supplement one another to yield 100 wt %,
as well as mixtures thereof.

The following may be used as active ingredients (A2) in the active ingredient complex (A).
native fibroin converted to a soluble form,
hydrolyzed and/or further derivatized fibroin, especially partially hydrolyzed fibroin, which contains as the main ingredient the amino acid sequence Ser-Gly-Ala-Gly-Ala-Gly,
the amino acid sequence Ser-Gly-Ala-Gly-Ala-Gly,
a mixture of the amino acids glycine, alanine and tyrosine and/or their methyl, propyl, isopropyl, butyl, isobutyl esters, the salts thereof such as hydrochlorides, sulfates, acetates, citrates, tartrates, where the glycine and/or its derivatives are present in this mixture in amounts of 20 to 60 wt %, alanine and its derivatives are present in amounts of 10 to 40 wt % and tyrosine and its derivatives are present in amounts of 0 to 25 wt %, with the provision that the amounts of these amino acids and/or their derivatives supplement one another to preferably 100 wt %,
as well as mixtures thereof.

Especially good care properties can be achieved if one of the two active ingredient components of the active ingredient complex (A) is used in the native form or at any rate in the solubilized form. It is also possible to use a mixture of several active ingredients (A1) and/or (A2).

It may be preferable for the two active ingredients (A1) and (A2) to be used in a ratio of 10:90 to 70:30, in particular 15:85 to 50:50 and most especially 20:80 to 40:60, based on their respective active ingredient contents in the inventive agents.

The derivatives of the hydrolyzates of serine and fibroin comprise both anionic and cationic protein hydrolyzates. The protein hydrolyzates of sericin and fibroin as well as the derivatives produced from them can be obtained from the corresponding proteins by chemical hydrolysis, in particular by alkaline or acidic hydrolysis, by enzymatic hydrolysis and/or a combination of the two types of hydrolysis. Hydrolysis of proteins usually yields a protein hydrolyzate with a molecular weight distribution from approximately 100 daltons up to several thousand daltons. Protein hydrolyzates of sericin and fibroin and/or their derivatives whose basic protein content has a molecular weight of 100 to 25,000 daltons, preferably 250 to 10,000 daltons are preferred. In addition, cationic protein hydrolyzates of sericin and fibroin also include quaternized amino acids and mixtures thereof. Quaternization of the protein hydrolyzates and/or amino acids is often performed by quaternary ammonium salts such as N,N-dimethyl-N-(n-alkyl)-N-(2-hydroxy-3-chloro-n-propyl)ammonium halides. In addition, the cationic protein hydrolyzates may also be further derivatized. Typical examples of cationic protein hydrolyzates and derivatives usable according to this invention may include the commercial products listed under the following INCI designations in the *International Cosmetic Ingredient Dictionary and Handbook* (seventh edition 1997, The Cosmetic, Toiletry, and Fragrance Association, 1101 17$^{th}$ Street, N.W., Suite 300, Washington, D.C. 20036-4702): cocodimonium hydroxypropyl hydrolyzed silk, cocodimonium hydroxypropyl silk amino acids, hydroxypropyltrimonium hydrolyzed silk, lauryidimonium hydroxypropyl hydrolyzed silk, steardimonium hydroxypropyl hydrolyzed silk, quaternium-79 hydrolyzed silk. Typical examples of the inventive anionic protein hydrolyzates and derivatives include the commercially products listed under the following INCI designations in the *International Cosmetic Ingredient Dictionary and Handbook* (seventh edition 1997, The Cosmetic, Toiletry, and Fragrance Association, 1101 17$^{th}$ Street, N.W., Suite 300, Washington, D.C. 20036-4702): potassium cocoyl hydrolyzed silk, sodium lauroyl hydrolyzed silk or sodium stearoyl hydrolyzed silk. Ultimately, the products that are commercially available under the following INCI designations may also be listed as typical examples of the derivatives of sericin and fibroin usable according to the invention: ethyl ester of hydrolyzed silk and hydrolyzed silk PG-propyl methylsilanediol. Also usable according to the invention, although not necessarily preferred, are the commercially available products with the INCI designations palmitoyl oligopeptide, palmitoyl pentapeptide-3, palmitoyl pentapeptide-2, acetyl hexapeptide-1, acetyl hexapeptide-3, copper tripeptide-1, hexapeptide-1, hexapeptide-2, MEA-hydrolyzed silk.

The effect of the active ingredient complex (A) can be further enhanced by addition of fatty substances. Fatty substances are understood to be fatty acids, fatty alcohols, natural and synthetic waxes, which may be present in solid form and in liquid form in aqueous dispersion, and natural and synthetic cosmetic oil components.

Protein hydrolyzates of plant origin, e.g. soy, almond, pea, potato and wheat protein hydrolyzates, for example, are available under the brand names Gluadin® (Cognis), DiaMin® (Diamalt), Lexein® (Inolex), Hydrosoy® (Croda), Hydrolupin® (Croda), Hydrosesame® (Croda), Hydrotritium® (Croda) and Crotein® (Croda).

Although the use of protein hydrolyzates as such is preferred, instead of them, amino acid mixtures obtained by other methods may optionally also be used. Likewise, the use of derivatives of protein hydrolyzates is also possible, e.g. in the form of their fatty acid condensation products. For example, such products are distributed under the brand names Lamepon® (Cognis), Lexein® (Inolex), Crolastin® (Croda), Crosilk® (Croda) or Crotein® (Croda).

The inventive teaching of course also includes all isomeric forms, such as cis and trans isomers, diastereomers and chiral isomers.

According to the invention, it is also possible to use a mixture of several protein hydrolyzates.

The protein hydrolyzates are present in the inventive agents, e.g. in concentrations of 0.01 wt % to 20 wt %, preferably from 0.05 wt % to 15 wt % and most particularly preferably in amounts of 0.05 wt % to 5 wt %, each based on the total preparation for use.

In addition, cationic surfactants are also suitable as a care substance from another class of compounds.

Preferred according to the invention are cationic surfactants of the quaternary ammonium type, the esterquat type and the amidoamine type. Preferred quaternary ammonium compounds include ammonium halides, in particular chlorides and bromides such as alkyltrimethylammonium chloride, dialkyldimethylammonium chlorides and trialkylmethylammonium chlorides, e.g. cetyltrimethylammonium chloride, stearyltrimethylammonium chloride, distearyldimethylammonium chloride, lauryldimethylammonium chloride, lauryldimethylbenzylammonium chloride and tricetylmethylammonium chloride as well as the imidazolium compounds known by the INCI designations quaternium-27 and quaternium-83. The long alkyl chains of the aforementioned surfactants preferably contain 10 to 18 carbon atoms.

The esterquats are known substances containing at least one ester function as well as at least one quaternary ammonium group as a structural element. Preferred esterquats are quaternized ester salts of fatty acids with triethanolamine, quaternized ester salts of fatty acids with diethanolalkylamines and quaternized ester salts of fatty acids with 1,2-dihydroxypropyldialkylamines. Such products are distributed under the brand names Stepantex®, Dehyquart® and Armocare®, for example. The products Armocare® VGH-70, an N,N-bis(2-palmitoyloxyethyl)dimethylammonium chloride as well as Dehyquart® F-75, Dehyquart® C-4046, Dehyquart® L80 and Dehyquart® AU-35 are examples of such esterquats.

The alkylamidoamines are usually synthesized by amidation of natural or synthetic fatty acids and fatty acids cuts with dialkylaminoamines. A compound from this substance group that is especially suitable according to the invention is the stearamidopropyldimethylamine available commercially under the designation Tegoamid® S18.

The cationic surfactants are preferably present in the inventive agent in amounts of 0.05 to 10 wt %, based on the total preparation for use. Amounts of 0.1 to 5 wt % are especially preferred.

Likewise, care polymers are also suitable as the care substance. It should be pointed out here that some care polymers also have film-forming and/or setting properties and therefore may also be listed among the suitable film-forming and/or setting polymers.

A first group of care polymers are the cationic polymers. Cationic polymers are understood to be polymers having in the main chain and/or in the side chain a group which may be "temporarily" or "permanently" cationic. Such polymers containing a cationic group independently of the pH of the agent are referred to as "permanently cationic" according to the invention. These are usually polymers having a quaternary nitrogen atom, e.g. in the form of an ammonium group. Preferred cationic groups include quaternary ammonium groups. In particular polymers in which the quaternary ammonium group is bonded by a $C_{1-4}$ hydrocarbon group to a polymer main chain synthesized from acrylic acid, methacrylic acid or derivatives thereof have proven to be especially suitable.

Homopolymers of the general formula (G1-I)

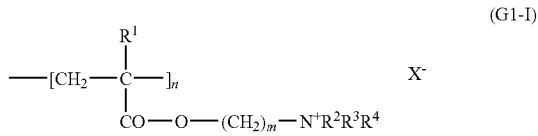

(G1-I)

in which $R^1$=H or $CH_3$, $R^2$, $R^3$ and $R^4$ are selected independently of one another from $C_{1-4}$ alky, alkenyl or hydroxyalkyl groups, m=1, 2, 3 or 4, n is a natural number and $X^-$ is a physiologically tolerable organic or inorganic anion as well as copolymers consisting essentially of the monomer units covered by formula (G1-I) as well as nonionic monomer units, are particularly preferably cationic polymers. Within the scope of these polymers, those preferred according to the invention are those for which at least one of the following conditions holds:

$R^1$ stands for a methyl group,
$R^2$, $R^3$ and $R^4$ stand for methyl groups,
m has the value 2.

Examples of physiologically tolerable counterions $X^-$ include halide ions sulfate ions, phosphate ions, methosulfate ions as well as organic ions such as lactate, citrate, tartrate and acetate ions. Halide ions are preferred, in particular chloride.

An especially preferred homopolymer is the optionally crosslinked poly(methacryloyloxyethyltrimethylammonium chloride) with the INCI designation polyquaternium-37. Crosslinking may, if desired, be accomplished with the help of olefinically polyunsaturated compounds, for example, divinylbenzene, tetraallyloxyethane, methylenebisacrylique acid amide, diallyl ether, polyallyl polyglyceryl ether or ally ethers of sugars or sugar derivatives such as erythritol, pentaerythritol, arabitol, mannitol, sorbitol, sucrose or glucose. Methylenebisacrylique acid amide is a preferred crosslinking agent.

The homopolymer is preferably used in the form of a nonaqueous polymer dispersion, which should have a polymer content of no less than 30 wt %. Such polymer dispersions are available under the brand names Salcare® SC 95 (approximately 50% polymer content, additional components: mineral oil (INCI designation: mineral oil) and tridecylpolyoxypropylene-polyoxyethylene ether (INCI designation: PPG-1 trideceth-6)) and Salcare® SC 96 (approximately 50% polymer content, additional components: mixture of diesters of propylene glycol with a mixture of caprylic acid and capric acid (INCI designation: propylene glycol dicaprylate/dicaprate) and tridecyl-polyoxy-propylene-polyoxyethylene ether (INCI designation: PPG-1 trideceth-6)).

Copolymers with monomer units according to formula (G1-I) preferably contain as nonionic monomer units acrylique acid amide, methacrylique acid amide, acrylic acid $C_{1-4}$ alkyl esters and methacrylic acid $C_{1-4}$ alkyl esters. Of these nonionic monomers, acrylique acid amide is especially preferred. These copolymers may also be crosslinked, as described above in the case of the homopolymers. A copolymer that is preferred according to the invention is the crosslinked acrylique acid amide-methacryloyloxyethyltrimethylammonium chloride copolymer. Such copolymers in which the monomers are present in a weight ratio of approximately 20:80 are commercially available as approximately 50% nonaqueous polymer dispersion under the brand name Salcare® SC 92.

Other preferred cationic polymers are, for example:

quaternized cellulose derivatives, such as those available commercially under the brand names Celquat® and Polymer JR®. The compounds Celquat® H 100, Celquat® L 200 and Polymer JR® 400 are preferably quaternized cellulose derivatives, cationic alkyl polyglycosides according to DE 44 13 686, cationized honey, e.g. the commercial product Honeyquat® 50, cationic guar derivatives such as in particular the products distributed under the brand names Cosmedia® guar and Jaguar®, polysiloxanes with quaternary groups such as the products available commercially as Q2-7224 (manufacturer: Dow Corning; a stabilized trimethylsilylamodimethicone), Dow Corning® 929 emulsion (containing a hydroxylamino-modified silicone, also known as amodimethicone), SM-2059 (manufacturer General Electric), SLM-55067 (manufacturer Wacker) and Abil® Quat 3270 and 3272 (manufacturer: Th. Goldschmidt), diquaternary polydimethylsiloxane, quaternium-80), polymeric dimethyldiallylammonium salts and their copolymers with esters and amides of acrylic acid and methacrylic acid. The products available commercially under the brand names Merquat® 100 (poly(dimethyldiallylammonium chloride)) and Merquat® 550 (dimethyldiallylammonium chloride acrylique acid amide copolymer) are examples of such cationic polymers, copolymers of vinylpyrrolidone with quaternized derivatives of dialkylaminoalkyl acrylate and methacrylate such as, for example, vinylpyrrolidone dimethylaminoethyl methacrylate copolymers quaternized with diethyl sulfate. Such compounds are available commercially under the brand names Gafquat® 734 and Gafquat® 755, vinylpyrrolidone-vinylimidazolium methochloride copolymers such as those offered under the brand names Luviquat® FC 370, FC 550, FC 905 and HM 552, quaternized polyvinyl alcohol, as well as the polymers with quaternary nitrogen atoms in the main polymer chain, known by the names polyquaternium-2, polyquaternium-17, polyquaternium-18 and polyquaternium-27.

The polymers known by the names polyquaternium-24 (commercial product, e.g. Quatrisoft® LM 200) may also be used as cationic polymers. The copolymers of vinylpyrrolidone may also be used according to this invention, such as those available as commercial products Copolymer 845 (manufacturer: ISP), Gaffix® VC 713 (manufacturer: ISP), Gafquat® ASCP 1011, Gafquat® HS 110, Luviquat® 8155 and Luviquat® MS 370.

Additional cationic polymers usable according to the invention are the so-called "temporarily cationic" polymers. These polymers usually contain an amino group, which is present as a quaternary ammonium group at a certain pH and thus is in cationic form. For example, chitosan and its derivatives such as the products available commercially under the brand names Hydagen® CMF, Hydagen® HCMF, Kytamer® PC and Chitolam® NB/101 are preferred.

Cationic polymers preferred for use according to this invention include cationic cellulose derivatives and chitosan and its derivatives, in particular the commercial products Polymer® JR 400, Hydagen® HCMF and Kytamer® PC, cationic guar derivatives, cationic honey derivatives, in particular the commercial product Honeyquat® 50, cationic alkyl polyglycosides according to DE 44 13 686 and polymers of the polyquaternium-37 type.

In addition, cationized protein hydrolyzates may be considered as cationic polymers, whereby the basic protein hydrolyzate on which it is based may originate from animals, e.g. from collagen, milk or keratin, from plants, e.g. from wheat, corn, rice, potatoes, soy or almonds, from marine life forms, e.g. from fish collagen or algae, or from protein hydrolyzates obtained by biotechnological methods. The protein hydrolyzates on which the cationic derivatives are based may be obtained from the corresponding proteins by chemical hydrolysis, in particular by alkaline hydrolysis or acidic hydrolysis, by enzymatic hydrolysis and/or a combination of the two types of hydrolysis. Hydrolysis of proteins usually yields a protein hydrolyzate with a molecular weight distribution of approximately 100 daltons up to several thousand daltons. Such cationic protein hydrolyzates whose fundamental protein content has a molecular weight of 100 up to 25,000 daltons, preferably 250 to 5000 daltons are preferred. In addition, cationic protein hydrolyzates are understood to include amino acids and mixtures thereof. Quaternization of the protein hydrolyzates or the amino acids is often performed by means of quaternary ammonium salts such as N,N-dimethyl-N-(n-alkyl)-N-(2-hydroxy-3-chloro-n-propyl)ammonium halides. In addition, the cationic protein hydrolyzates may also be further derivatized. Typical examples of the inventive cationic protein hydrolyzates and derivatives include the commercially available products listed under the INCI designations in the *International Cosmetic Ingredient Dictionary and Handbook* (seventh edition 1997, The Cosmetic, Toiletry, and Fragrance Association, 1101 17$^{th}$ Street, N.W., Suite 300, Washington, D.C. 20036-4702): cocodimonium hydroxypropyl hydrolyzed collagen, cocodimonium hydroxypropyl hydrolyzed casein, cocodimonium hydroxypropyl hydrolyzed collagen, cocodimonium hydroxypropyl hydrolyzed hair keratin, cocodimonium hydroxypropyl hydrolyzed keratin, cocodimonium hydroxypropyl hydrolyzed rice protein, cocodimonium hydroxypropyl hydrolyzed soy protein, cocodimonium hydroxypropyl hydrolyzed wheat protein, hydroxypropyl arginine lauryl/myristyl ether HCl, hydroxypropyltrimonium gelatin, hydroxypropyltrimonium hydrolyzed casein, hydroxypropyltrimonium hydrolyzed collagen, hydroxypropyltrimonium hydrolyzed conchiolin protein, hydroxypropyltrimonium hydrolyzed keratin, hydroxypropyltrimonium hydrolyzed rice bran protein, hydroxypropyltrimonium hydrolyzed soy protein, hydroxypropyltrimonium hydrolyzed vegetable protein, hydroxypropyltrimonium hydrolyzed wheat protein, hydroxypropyltrimonium hydrolyzed wheat protein/siloxysilicate, laurdimonium hydroxypropyl hydrolyzed soy protein, laurdimonium hydroxypropyl hydrolyzed wheat protein, laurdimonium hydroxypropyl hydrolyzed wheat protein/siloxysilicate, lauryldimonium hydroxypropyl hydrolyzed casein, lauryldimonium hydroxypropyl hydrolyzed collagen, lauryldimonium hydroxypropyl hydrolyzed keratin, lauryldimonium hydroxypropyl hydrolyzed soy protein, steardimonium hydroxypropyl hydrolyzed casein, steardimonium hydroxypropyl hydrolyzed collagen, steardimonium hydroxypropyl hydrolyzed keratin, steardimonium hydroxypropyl hydrolyzed rice protein, steardimonium hydroxypropyl hydrolyzed soy protein, steardimonium hydroxypropyl hydrolyzed vegetable protein, steardimonium hydroxypropyl hydrolyzed wheat protein, steartrimonium hydroxypropyl hydrolyzed collagen, quaternium-76 hydrolyzed collagen, quaternium-79 hydrolyzed collagen, quaternium-79 hydrolyzed keratin, quaternium-79 hydrolyzed milk protein, quaternium-79 hydrolyzed soy protein, quaternium-79 hydrolyzed wheat protein.

The cationic protein hydrolyzates and derivatives on a plant basis are most especially preferred.

Amphoteric polymers preferred for use here include polymers composed essentially of
(a) monomers with quaternary ammonium groups of general formula (II)

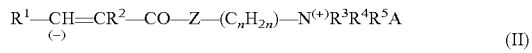

in which $R^1$ and $R^2$, independently of one another, stand for hydrogen or a methyl group, and $R^3$, $R^4$ and $R^5$, independently of one another, stand for an alkyl group with one to four carbon atoms, Z stands for an NH group or an oxygen atom, n stands for an integer from 2 to 5 and $A^{(-)}$ is the anion of an organic or inorganic acid and
(b) monomeric carboxylic acids of general formula (III)

in which $R^6$ and $R^7$, independently of one another, stand for hydrogen or a methyl group.

These compounds may be used according to this invention either directly or in salt form obtained by neutralization of the polymers, e.g. with an alkali hydroxide. Most especially preferred are polymers in which monomers of type (a) are used, wherein $R^3$, $R^4$ and $R^5$ are methyl groups, Z is an NH group and $A^{(-)}$ is a halide ion, a methoxysulfate ion or an ethoxysulfate ion; acrylamidopropyltrimethylammonium chloride is an especially preferred monomer (a). Acrylic acid is preferred as monomer (b) for the aforementioned polymers.

The agents according to the invention preferably contain the cationic and/or amphoteric care polymers in an amount of 0.01 to 5 wt %, in particular in an amount of 0.1 to 2 wt %, each based on the total preparation for use.

The inventive agent may also contain at least one vitamin, a provitamin, a vitamin precursor and/or one of their derivatives as the care substance.

Vitamins, provitamins and vitamin precursors, which usually are assigned to the groups A, B, C, E, F and H, are preferred according to the invention.

The group of substances designated as vitamin A includes the retinal (vitamin $A_1$) and 3,4-didehydroretinal (vitamin $A_2$). β-Carotene is the provitamin of retinol. According to the invention, for example, vitamin A acid and its esters, vitamin A aldehyde and vitamin A alcohol as well as its esters such as the palmitate and the acetate may be considered as the vitamin A component. The agents preferably contain the vitamin A component in amounts of 0.05-1 wt %, based on the total preparation for use.

The vitamin B group of the vitamin B complex includes, for example:

Vitamin $B_1$ (thiamine),
Vitamin $B_2$ (riboflavin),
Vitamin $B_3$. This designation often includes the compounds nicotinic acid and nicotinamide (niacinamide). According to the invention, nicotinamide. which is preferably contained in the inventive agents in amounts of 0.05 to 1 wt %, based on the total preparation for use, is preferred according to the invention.
Vitamin $B_5$ (pantothenic acid, panthenol and pantolactone). Within the scope of this group, panthenol and/or pantolactone is preferred for use here. Derivatives of panthenol that are usable according to the invention include in particular the esters and ethers of panthenol and cationically derivatized panthenols. Individual representatives include, for example, panthenol triacetate, panthenol monoethyl ether and its monoacetate as well as cationic panthenol derivatives. The aforementioned compounds of the vitamin $B_5$ type are preferably contained in the inventive agents in amounts of 0.05-10 wt %, based on the total preparation for use. Amounts of 0.1-5 wt % are especially preferred.
Vitamin $B_6$ (pyridoxine as well as pyridoxamine and pyridoxal). Said compounds of the vitamin $B_6$ type are preferably contained in the inventive agents in amounts of 0.01-5 wt %, based on the total preparation for use. Amounts of 0.05-1 wt % are especially preferred.
Vitamin C (ascorbic acid). Vitamin C is preferably used in the inventive agents in amounts of 0.1 to 3 wt %, based on the total preparation for use. Use in the form of palmitic acid ester, glucosides or phosphates may be preferred. Use in combination with tocopherols may also be preferred.
Vitamin E (tocopherols, in particular α-tocopherol). Tocopherol and its derivatives, including in particular the esters such as the acetate, the nicotinate, the phosphate and the succinate, are preferably contained in the inventive agents in amounts of 0.05-1 wt %, based on the total preparation for use.
Vitamin F. The term "vitamin F" is usually understood to include essential fatty acids, in particular linoleic acid, linolenic acid and arachidonic acid.
Vitamin H. The compound (3aS,4S,6aR)-2-oxohexahydrothienol[3,4-d]-imidazole-4-valeric acid is known as vitamin H, but in the meantime the trivial name biotin has become popular for this compound. Biotin is preferably contained in the inventive agents in amounts of 0.0001 to 1.0 wt %, in particular in amounts of 0.001 to 0.01 wt %, each based on the total preparation for use.

The inventive agents preferably contain vitamins, provitamins and vitamin precursors from the groups A, B, C, E and H.

Panthenol, pantolactone, pyridoxine and its derivatives as well as nicotinamide and biotin are especially preferred.

D-Panthenol, optionally in combination with at least one of the aforementioned silicone derivatives, is most especially preferred as a care substance.

Like the addition of glycerol and/or propylene glycol, the addition of panthenol increases the flexibility of the polymer film formed when using the inventive agent. Thus, if an especially flexible hold is desired, the inventive agents may contain panthenol instead of or in addition to glycerol. In a preferred embodiment, the inventive agents contain panthenol, preferably in an amount of 0.05 to 10 wt %, particularly preferably 0.1-5 wt %, each based on the total agent.

The inventive agents may also contain at least one plant extract as a care substance.

These extracts are usually produced by extraction of the whole plant. However, in individual cases, it may also be preferable to prepare the extracts exclusively from the flowers and/or leaves of the plants.

With regard to the plant extracts preferred according to the invention, reference is made in particular to the extracts listed in the table beginning on page 44 of the third edition of the *Guideline for Declaration of Ingredients of Cosmetic Agents*, published by Industrieverband Körperpflege—und Waschmittel e.V. [Industrial Association for Body Care Agents and Detergents] (IKW) in Frankfurt.

According to the invention, especially preferred are the extracts of green tea, oak bark, stinging nettle, witch hazel, hops, henna, chamomile, burdock root, horsetail, hawthorn, lime blossom, almond, aloe vera, spruce needle, chestnut, sandalwood, common juniper, coconut, mango, apricot, lemon, wheat, kiwi, melon, orange, grapefruit, sage, rosemary, birch, mallow, lady's smock, creeping thyme, yarrow, thyme, balm, spiny rest harrow, coltsfoot, hibiscus, meristem, ginseng and ginger root.

Especially preferred are the extracts of green tea, oak bark, stinging nettle, witch hazel, hops, chamomile, burdock root, horsetail, lime blossom, almond, aloe vera, coconut, mango, apricot, lemon, wheat, kiwi, melon, orange, grapefruit, sage, rosemary, birch, lady's smock, creeping thyme, yarrow, spiny rest harrow, meristem, ginseng and ginger root.

Most especially suitable are the extracts of green tea, almond, aloe vera, coconut, mango, apricot, lemon, wheat, kiwi and melon.

Water, alcohols and mixtures therefore may be used as the extracting agents to produce the plant extracts listed. Of the alcohols, low alcohols such as ethanol and isopropanol, but in particular polyvalent alcohols such as ethylene glycol and propylene glycol are preferred, both as the sole extracting agent and also in mixture with water. Plant extracts based on water/propylene glycol in a ratio of 1:10 to 10:1 have proven especially suitable.

According to the invention, the plant extracts may be used in both pure form and in diluted form. If they are used in diluted form, they usually contain approximately 2-80 wt % active substance and the extracting agent or extracting agent mixture used to produce them as the solvent.

In addition, it may be preferable to use mixtures of several plant extracts, in particular two different plant extracts, in the inventive agents.

In addition, a number of carboxylic acids are suitable as the care substance.

In the sense of the invention, short-chain carboxylic acids may be advantageous in particular. Short-chain carboxylic acids and their derivatives in the sense of the invention are understood to be carboxylic acids, which may be saturated or unsaturated and/or linear or branched or cyclic and/or aromatic and/or heterocyclic and have a molecular weight of less than 750. In the sense of the invention, saturated or unsaturated, linear or branched carboxylic acids with a chain length of one to sixteen carbon atoms in the chain are preferred, and those having a chain length of one to twelve carbon atoms in the chain are most especially preferred.

The short-chain carboxylic acids in the sense of the invention may have one, two, three or more carboxyl groups. Preferred carboxylic acids in the sense of the invention are those having several carboxyl groups, in particular di- and tricarboxylic acids. The carboxyl groups may be partially or entirely present as the ester, acid anhydride, lactone, amide, imidic acid, lactam, lactim, dicarboximide, carbohydrazide, hydrazone, hydroxame, hydroxime, amidine, amidoxime, nitrile, phosphonic ester or phosphate ester. The carboxylic acids usable according to the invention may of course be substituted along the carbon chain or the ring structure. The substituents of the carboxylic acids usable according to the invention include, for example, $C_1$-$C_8$ alkyl, $C_2$-$C_8$ alkenyl, aryl, aralkyl and aralkenyl, hydroxymethyl, $C_2$-$C_8$ hydroxyalkyl, $C_2$-$C_8$ hydroxyalkenyl, aminomethyl, $C_2$-$C_8$ aminoalkyl, cyano, formyl, oxo, thioxo, hydroxy, mercapto, amino, carboxyl or imino groups. Preferred substituents are $C_1$-$C_8$ alkyl, hydroxymethyl, hydroxyl, amino and carboxyl groups. Especially preferred are substituents in a position. Most especially preferred substituents are hydroxyl, alkoxy and amino groups, where the amino function may optionally be further substituted by alkyl, aryl, aralkyl and/or alkenyl radicals. The phosphonic and phosphate esters are also preferred carboxylic acid derivatives.

Examples of carboxylic acids usable according to the invention include formic acid, acetic acid, propionic acid, butyric acid, isobutyric acid, valeric acid, isovaleric acid, pivalic acid, oxalic acid, malonic acid, succinic acid, glutaric acid, glyceric acid, glyoxylic acid, adipic acid, pimelic acid, suberic acid, azelaic acid, sebacic acid, propiolic acid, crotonic acid, isocrotonic acid, elaidic acid, maleic acid, fumaric acid, muconic acid, citraconic acid, mesaconic acid, camphoric acid, benzoic acid, o-, m- and p-phthalic acid, naphthoic acid, toluic acid, hydratropic acid, atropic acid, cinnamic acid, isonicotinic acid, nicotinic acid, bicarbamic acid, 4,4'-dicyano-6,6'-binicotinic acid, 8-carbamoyloctanoic acid, 1,2,4-pentanetricarboxylic acid, 2-pyrrolecarboxylic acid, 1,2,4,6,7-naphthalenepentaacetic acid, malonaldehydic acid, 4-hydroxyphthalamic acid, 1-pyrazolecarboxylic acid, gallic acid or propanetricarboxylic acid, a dicarboxylic acid selected from the group formed by compounds of the general formula (N-I):

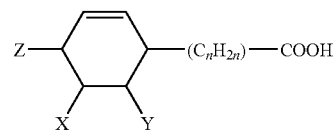

in which Z stands for a linear or branched alkyl group or alkenyl group with four to twelve carbon atoms, n stands for a number from 4 to 12 and one of the two groups X and Y stands for a COOH group and the other stands for hydrogen or a methyl or ethyl radical, dicarboxylic acids of general formula (N-I), which additionally have one to three methyl or ethyl substituents on the cyclohexene ring, and dicarboxylic acids that are formally made up from the dicarboxylic acids according to formula (N-I) by addition of one molecule of water at the double bond in the cyclohexene ring.

Dicarboxylic acids of formula (N-I) are known in the literature. For example, a synthesis process is described in U.S. Pat. No. 3,753,968.

The dicarboxylic acids of formula (N-I) may be synthesized, for example, by reacting polyunsaturated dicarboxylic acids with unsaturated monocarboxylic acids in the form of a Diels-Alder cyclization. This will usually start with a polyunsaturated fatty acid as the dicarboxylic acid component. Linoleic acid, which is accessible from natural fats and oils, is preferred. Acrylic acid in particular is preferred as the monocarboxylic acid component, but methacrylic and crotonic acid, for example, are also preferred. Reactions according to Diels-Alder usually yield isomer mixtures in which one component is present in excess. These isomer mixtures may be used according to the invention as well as the pure compounds.

In addition to the preferred dicarboxylic acids according to formula (N-I), dicarboxylic acids that differ from the compounds according to formula (N-I) by one to three methyl or ethyl substituents on the cyclohexyl ring or which are made up from these compound formally by addition of one molecule of water at the double bond of the cyclohexene ring may also be used according to the invention.

The dicarboxylic acid (mixture) formed by reaction of linoleic acid with acrylic acid has proven to be especially effective according to the invention. This is a mixture of 5- and 6-carboxy-4-hexyl-2-cyclohexene-1-octanoic acid. Such compounds are available commercially under the brand names Westvaco Diacid® 1550 and Westvaco Diacid® 1595 (manufacturer: Westvaco).

In addition to the short-chain carboxylic acids mentioned above as examples, their physiologically tolerable salts may also be used according to the invention. Examples of such salts include the alkali, alkaline earth and zinc salts as well as ammonium salts, which are also understood to include within the scope of the present patent application the mono-, di- and trimethyl-, -ethyl- and hydroxyethylammonium salts. Within the scope of the invention, however, acids neutralized with amino acids that give a alkaline reaction, for example, arginine, lysine, ornithine and histidine, are most especially preferred for use here. In addition, it may be preferable for formulation reasons to select the carboxylic acids from the water-soluble representatives, in particular the water-soluble salts.

Furthermore, it is preferable according to the invention to use 2-pyrrolidinone-5-carboxylic acids and their derivatives as carboxylic acids. The sodium, potassium, calcium, magnesium or ammonium salts are especially preferred, where the ammonium ion also has one to three $C_1$ to $C_4$ alkyl groups in addition to hydrogen. The sodium salt is most especially preferred. The quantities used in the inventive agents preferably amount to 0.05 to 10 wt %, based on the total preparation for use, particularly preferably 0.1 to 5 wt % and in particular preferably 0.1 to 3 wt %.

In addition, it is preferable according to the invention to use hydroxycarboxylic acids, and here again, in particular to use the dihydroxy-, trihydroxy- and polyhydroxycarboxylic acids as well as the dihydroxy-, trihydroxy- and polyhydroxydi-, tri- and polycarboxylic acids. It has been found here that in addition to the hydroxycarboxylic acids, the hydroxycarboxylic acid esters as well as the mixtures of hydroxycarboxylic acids and their esters as well as polymeric hydroxycarboxylic acids and their esters may be most especially preferred. Preferred hydroxycarboxylic acid esters include, for example, the full esters of glycolic acid, lactic acid, malic acid, tartaric acid or citric acid. Other fundamentally suitable hydroxycarboxylic acid esters include the esters of β-hydroxypropionic acid, tartronic acid, D-gluconic acid, saccharic acid, mucic acid or glucuronic acid. Primary, linear or branched aliphatic alcohols with eight to 22 carbon atoms, for example, fatty alcohols or synthetic fatty alcohols are suitable as the alcohol component of these esters, The esters of $C_{12}$-$C_{15}$ fatty alcohols are especially preferred. Esters of this type are commercially available, e.g. under the brand name Cosmacol® from EniChem, Augusta Industriale. Especially preferred polyhydroxypolycarboxylic acids are polylactic acid and polytartaric acid as well as their esters.

In addition, ectoin or ectoin derivatives, allantoin, taurine and bisabolol are suitable as care substances.

According to the invention, the term "ectoin and ectoin derivatives" is understood to include compounds of the formulas (IV)

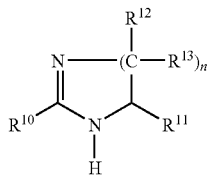
(IVa)

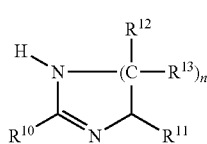
(IVb)

and/or their physiologically tolerable salts and/or an isomeric or stereoisomeric form, in which $R^{10}$ stands for a hydrogen atom, a branched or unbranched $C_1$-$C_4$ alkyl radical or a $C_2$-$C_4$ hydroxyalkyl radical, $R^{11}$ stands for a hydrogen atom, a $COOR^{14}$ group or a $CO(NH)R^{14}$ group, where $R^{14}$ may stand for a hydrogen atom, a $C_1$-$C_4$ alkyl radical, an amino acid radical, a dipeptide radical or a tripeptide radical, $R^{12}$ and $R^{13}$ independently of one another stand for a hydrogen atom, a $C_1$-$C_4$ alkyl radical or a hydroxyl group, with the provision that both radicals may not stand for a hydroxyl group at the same time, and n stands for an integer from 1 to 3.

Suitable physiologically tolerable salts of the general compounds according to formulas (IVa) or (IVb) include, for example, the alkali, alkaline earth, ammonium, triethylamine or tris-(2-hydroxyethyl)amine salts as well as those derived from the reaction of compounds according to formulas (IVa) or (IVb) with organic and inorganic acids such as hydrochloric acid, phosphoric acid, sulfuric acid, branched or unbranched, substituted or unsubstituted (e.g. by one or more hydroxyl groups) $C_1$-$C_4$ mono- or dicarboxylic acids, aromatic carboxylic acids and sulfonic acids, such as acetic acid, citric acid, benzoic acid, maleic acid, fumaric acid, tartaric acid and p-toluenesulfonic acid. Examples of especially preferred physiologically tolerable salts include the Na, K, Mg, Ca and ammonium salts of the compounds according to formula (IVa) or (IVb) as well as the salts derived by reaction of compounds according to formula (IVa) or (IVb) with hydrochloric acid, acetic acid, citric acid and benzoic acid.

Isomeric or stereoisomeric forms of the compounds according to formula (IVa) or (IVb) are understood according to the invention to include all the optical isomers, diastereomers, racemates, zwitterions, cations or mixtures thereof that occur.

The term amino acid is understood to include the stereoisomeric forms, e.g. D and L forms of the following compounds: asparagine, arginine, aspartic acid, glutamine, glutamic acid, β-alanine, γ-aminobutyrate, $N_\epsilon$-acetyllysine, $N_\delta$-acetylornithine, $N_\gamma$-acetyldiaminobutyrate, $N_\alpha$-acetyldiaminobutyrate, histidine, isoleucine, leucine, methionine, phenylalanine, serine, threonine and tyrosine.

L-Amino acids are preferred. Amino acid radicals are derived from the corresponding amino acids. The following amino acid radicals are preferred: Gly, Ala, Ser, Thr, Val, R-Ala, γ-aminobutyrate, Asp, Glu, Asn, Aln, $N_\epsilon$-acetyllysine, $N_\delta$-acetylornithine, $N_\gamma$-acetyldiaminobutyrate, $N_\alpha$-acetyldiaminobutyrate.

The abbreviated notation for amino acids is based on the notation that is customary in general. The di- or tripeptide radicals are acid amides according to their chemical nature and decompose in hydrolysis into two or three amino acids. The amino acids in the di- or tripeptide radical are linked by amide bonds.

With regard to the synthesis of the di- and tripeptide radicals, reference is made explicitly to EP 0 671 161 A1 by the company Marbert. Examples of di- and tripeptide radicals can be found in the disclosure of EP 0 671 161 A1.

Examples of $C_1$-$C_4$ alkyl groups in the compounds of formula (IV) include methyl, ethyl, n-propyl, isopropyl, n-butyl, isobutyl and tert-butyl. Preferred alkyl groups are methyl and ethyl. Methyl is an especially preferred alkyl group. Preferred $C_2$-$C_4$ hydroxyalkyl groups are the groups 2-hydroxyethyl, 3-hydroxypropyl or 4-hydroxybutyl. 2-Hydroxyethyl is an especially preferred hydroxyalkyl group.

The inventive agents contain these care substances preferably in amounts of 0.001 to 2 wt %, in particular from 0.01 to 0.5 wt %, each based on the total preparation for use.

Monosaccharides and/or oligosaccharides may also be used as the care substance in the inventive agents.

Both monosaccharides and oligosaccharides such as cane sugar, lactose and raffinose may be used. The use of monosaccharides is preferred according to the invention. Of the monosaccharides, compounds containing five or six carbon atoms are again preferred.

Suitable pentoses and hexoses include, for example, ribose, arabinose, xylose, lyxose, allose, altrose, glucose, mannose, gulose, idose, galactose, talose, fucose and fructose. Arabinose, glucose, galactose and fructose are preferred carbohydrate for use here; most especially preferred for use here is glucose, which is suitable in both the D-(+)- and L-(−)-configurations or as a racemate.

In addition, derivatives of these pentoses and hexoses as well as the corresponding aldonic and uronic acids (saccharic acids), sugar alcohols and glycosides may also be used according to the invention. Preferred saccharic acids include gluconic acid, glucuronic acid, saccharic acid, mannosaccharic acid and mucic acid. Preferred sugar alcohols include sorbitol, mannitol and dulcitol. Preferred glycosides are the methyl glucosides.

Since the starting mono- and/or oligosaccharides are usually obtained from natural raw materials such as starch, they usually have the configurations corresponding to these raw materials (e.g. D-glucose, D-fructose and D-galactose).

The monosaccharides and/or oligosaccharides are preferably present in the inventive agents in an amount of 0.1 to 8 wt %, particularly preferably 1 to 5 wt %, based on the total preparation for use.

The agent may also contain at least one lipid as a care substance.

Lipids suitable according to the invention are phospholipids, for example, soy lecithin, egg lecithin and cephalins as well as the substances known by the INCI designations linoleamidopropyl PG-dimonium chloride phosphate, cocamidopropyl PG-dimonium chloride phosphate and stearamidopropyl PG-dimonium chloride phosphate. These are distributed by the company Mona, for example, under the brand names Phospholipid EFA®, Phospholipid PTC® and Phospholipid SV®.

The inventive agents preferably contain the lipids in amounts of 0.01-10 wt %, in particular 0.1-5 wt %, based on the total preparation for use.

Oil substances are also suitable as the care substance.

The natural and synthetic cosmetic oil substances include, for example:

Vegetable oils. Examples of such oils include sunflower oil, olive oil, soy oil, rapeseed oil, olive oil, jojoba oil, orange oil, wheat germ oil, peach kernel oil and the liquid fractions of coconut oil. However, other triglyceride oils such as the liquid fractions of beef tallow and synthetic triglyceride oils are also suitable.

Liquid paraffin oils, isoparaffin oils and synthetic hydrocarbons as well as di-n-alkyl ethers with a total of between 12 and 36 carbon atoms, in particular 12 to 24 carbon atoms such as, for example, di-n-octyl ether, di-n-decyl ether, di-n-nonyl ether, di-n-undecyl ether, di-n-dodecyl ether, n-hexyl-n-octyl ether, n-octyl-n-decyl ether, n-decyl-n-undecyl ether, n-undecyl-n-dodecyl ether and n-hexyl-n-undecyl ether as well as di-tert-butyl ether, diisopentyl ether, di-3-ethyldecyl ether, tert-butyl-n-octyl ether, isopentyl-n-octyl ether and 2-methylpentyl-n-octyl ether. The compounds 1,3-di-(2-ethylhexyl)cyclohexane (Cetiol® S) and di-n-octyl ether (Cetiol® OE) that are available as commercial products may also be preferred.

Ester oils. Ester oils are understood to include the esters of $C_6$-$C_{30}$ fatty acids with $C_2$-$C_{30}$ fatty alcohols. The monoesters of fatty acids with alcohols with two to 24 carbon atoms are preferred. Examples of fatty acid fractions in the esters used here are caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachic acid, gadoleic acid, behenic acid and erucaic acid as well as their technical-grade mixtures, which are obtained in pressurized cracking of natural fats and oils, in the oxidation of aldehydes from Roelen's oxo synthesis or dimerization of unsaturated fatty acids. Examples of the fatty alcohol fractions in the ester oils include isopropyl alcohol, hexyl alcohol, n-octyl alcohol, 2-ethylhexyl alcohol, n-decyl alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol as well as their technical-grade mixtures, which are obtained, for example, in high-pressure hydrogenation of technical-grade methyl esters based on fats and oils or aldehydes from Roelen's oxo synthesis as well as monomer fractions in dimerization of unsaturated fatty alcohols. Especially preferred according to the invention are isopropyl myristate (Rilanit® IPM), isononanoic acid $C_{16-18}$ alkyl ester (Cetiol® SN), 2-ethylhexyl palmitate (Cegesoft® 24), stearic acid 2-ethylhexyl ester (Cetiol® 868), cetyl oleate, glycerol tricaprylate, coconut fatty alcohol caprinate/caprylate (Cetiol® LC), n-butyl stearate, oleyl erucate (Cetiol® J 600), isopropyl palmitate (Rilanit® IPP), oleyl oleate (Cetiol®), lauric acid hexyl ester (Cetiol® A), di-n-butyl adipate (Cetiol® B), myristyl myristate (Cetiol® MM), cetearyl isononanoate (Cetiol® SN), oleic acid decyl ester (Cetiol® V).

Dicarboxylic acid esters such as di-n-butyl adipate, di(2-ethylhexyl) adipate, di(2-ethylhexyl) succinate and diisotridecyl acetate as well as diol esters such as ethylene glycol dioleate, ethylene glycol diisotridecanoate, propylene glycol di(2-ethylhexanoate), propylene glycol diisostearate, propylene glycol dipelargonate, butanediol diisostearate, neopentyl glycol dicaprylate.

Symmetrical, asymmetrical or cyclic esters of carbonic acid with fatty alcohols, described, for example, in Unexamined German Patent DE-OS 197 56 454, glycerol carbonate or dicaprylyl carbonate (Cetiol® CC).

Trifatty acid esters of saturated and/or unsaturated linear and/or branched fatty acids with glycerol.

Fatty acid partial glycerides, which are understood to include monoglycerides, diglycerides and their technical-grade mixtures. In the use of technical products, small quantities of triglycerides may still be present due to the synthesis process. The partial glycerides preferably conform to the formulas (D4-I)

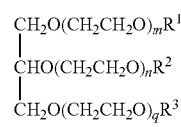

(D4-I)

in which $R^1$, $R^2$ and $R^3$ independently of one another stand for hydrogen or a linear or branched, saturated and/or unsaturated acyl radical with six to 22 carbon atoms, preferably twelve to eighteen carbon atoms, with the provision that at least one of these groups stands for an acyl radical and at least one of these groups stands for hydrogen. The sum (m+n+q) stands for 0 or numbers from 1 to 100, preferably for 0 or 5 to 25. $R^1$ preferably stands for an acyl radical, and $R^2$ and $R^3$ stand for hydrogen and the sum (m+n+q) is 0. Typical examples include mono- and/or diglycerides based on caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachic acid, gadoleic acid, behenic acid and erucaic acid as well as their technical-grade mixtures. Oleic acid monoglycerides are preferably used.

The amount of the natural and synthetic cosmetic oil substances used in the inventive agents usually amounts to 0.1-30 wt %, based on the total preparation for use, preferably 0.1-20 wt % and in particular 0.1-15 wt %.

The agent may also contain an enzyme as a care substance. According to the invention, especially preferred enzymes are selected from a group made up from proteases, lipases, transglutaminases, oxidases and peroxidases.

Pearl extracts are also suitable as the care substance.

Pearls from oysters essentially consist of organic and inorganic calcium salts, trace elements and proteins. Pearls are easily obtained from cultured oysters. Oysters can be cultured in both fresh water and sea water. This may affect the ingredients of the pearls. Preferred according to the invention is a pearl extract originating from oysters cultured in sea water, i.e. salt water. The pearls largely consist of aragonite (calcium carbonate), conchiolin and an albuminoid. The latter ingredients are proteins. In addition, pearls also contain sodium and magnesium salts, inorganic silicon compounds as well as phosphates.

To produce the pearl extract, the pearls are pulverized. Then the pulverized pearls are extracted by conventional methods. Water, alcohols and mixtures thereof may be used as extracting agents to produce the pearl extracts. Water is understood to include both demineralized water and sea water. Of the alcohols, low alcohols such as ethanol and isopropanol are preferred, but in particular polyvalent alcohols such as glycerol, diglycerol, triglycerol, polyglycerol, ethylene glycol, propylene glycol and butylene glycol are preferred, both as the sole extracting agent and also in mixture with demineralized water or sea water. Pearl extracts based on water/glycerol mixtures have proven to be especially suitable. Depending on the extraction conditions, the pearl proteins (conchiloin and albuminoid) are present largely in a native state or are already partially or largely in the form of protein hydrolyzates. A pearl extract in which conchiloin and albuminoid are already partially hydrolyzed is preferred. The essential amino acids of these proteins are glutamic acid, serine, alanine, glycine, aspartic acid and phenylalanine. In another especially preferred embodiment, it may be advantageous if the pearl extract is additionally enriched with at least one or more of these amino acids. In the most preferred embodiment, the pearl extract is enriched with glutamic acid, serine and leucine. In addition, depending on the extraction conditions, in particular depending on the choice of the extracting agent, a more or less large amount of minerals and trace elements will be found in the extract. A preferred extract contains organic and/or inorganic calcium salts as well as magnesium and sodium salts, inorganic silicon compounds and/or phosphates. An especially preferred pearl extract contains at least 75%, preferably 85%, particularly preferably 90% and most particularly preferably 95% of all ingredients of the naturally occurring pearls. Examples of pearl extracts usable according to the invention include the commercial products Pearl Protein Extract BG® or Crodarom® Pearl.

The pearl extracts described previously are preferably present in an amount of at least 0.01 to 20 wt %. Extract amounts of 0.01 to 10 wt % are preferred, most particularly preferably amounts of 0.01 to 5 wt %, based on the total preparation for use.

Although each of the care substances listed yields a satisfactory result even alone, the scope of the present invention also includes all embodiments in which the agent contains multiple care substances even from different groups.

By adding a UV filter, the agents themselves as well as the treated fibers may be protected from the harmful effects of UV radiation. Therefore, at least one UV filter is preferably added to the agent. Suitable UV filters are not subject to any general restrictions with regard to their structure and their physical properties. Instead, all UV filters that can be used in the cosmetics field and which have an absorption maximum in the UVA range (315-400 nm), in the UVB range (280-315 nm) or in the UVC range (<280 nm) are suitable. UV filters with an absorption maximum in the UVB range, in particular in the range from approximately 280 nm to approximately 300 nm are especially preferred.

The UV filters preferred according to the invention may be selected, for example, from substituted benzophenones, p-aminobenzoic acid esters, diphenylacrylic acid esters, cinnamic esters, salicylic acid esters, benzimidazoles and o-aminobenzoic acid esters.

Examples of UV filters usable according to the invention include 4-aminobenzoic acid, N,N, N-trimethyl-4-(2-oxoborn-3-ylidenemethyl)aniline methyl sulfate, 3,3,5-trimethylcyclohexyl salicylate (homosalate), 2-hydroxy-4-methoxybenzophenone (benzophenone-3; Uvinul® M 40, Uvasorb® MET, Neo Heliopan® BB, Eusolex® 4360), 2-phenylbenzimidazole-5-sulfonic acid and their potassium, sodium and triethanolamine salts (phenylbenzimidazole sulfonic acid; Parsol® HS; Neo Heliopan® Hydro), 3,3'-(1,4-phenylene-dimethylene)-bis(7,7-dimethyl-2-oxobicyclo[2.2.1]hept-1-ylmethanesulfonic acid) and its salts, 1-(4-tert-butylphenyl)-3-(4-methoxyphenyl)-propane-1,3-dione (butylmethoxydibenzoylmethane; Parsol® 1789, Eusolex® 9020), α-(2-oxoborn-3-ylidene)toluene-4-sulfonic acid and its salts, ethoxylated 4-aminobenzoic acid ethyl ester (PEG-25 PABA; Uvinul® P 25), 4-dimethylaminobenzoic acid 2-ethylhexyl ester (octyl dimethyl PABA; Uvasorb® DMO, Escalol® 507, Eusolex® 6007), salicylic acid 2-ethylhexyl ester (octyl salicylate; Escalol® 587, Neo Heliopan® OS, Uvinul® O18), 4-methoxycinnamic acid isopentyl ester (isoamyl p-methoxycinnamate; Neo Heliopan® E 1000), 4-methoxycinnamic acid 2-ethylhexyl ester (octyl methoxycinnamate; Parsol® MCX, Escalol® 557, Neo Heliopan® AV), 2-hydroxy-4-methoxybenzophenone-5-sulfonic acid and their sodium salts (benzophenone-4; Uvinul® MS 40; Uvasorb® S 5), 3-(4'-methylbenzylidene)-D,L-camphor (4-methylbenzylidene camphor; Parsol® 5000, Eusolex® 6300), 3-benzylidenecamphor (3-benzylidenecamphor), 4-isopropylbenzyl salicylate, 2,4,6-trianilino-(p-carbo-2'-ethylhexyl-1'-oxy)-1,3,5-triazine, 3-imidazol-4-ylacrylic acid and its ethyl ester, polymers of N-{(2 and 4)-[2-oxoborn-3-ylidenemethyl]benzyl}acrylique acid amide, 2,4-dihydroxybenzophenone (benzophenone-1; Uvasorb® 20H, Uvinul® 400), 1,1'-diphenylacrylonitrilic acid 2-ethylhexyl ester (octocrylene; Eusolex® OCR, Neo Heliopan® Type 303, Uvinul® N 539 SG), o-aminobenzoic acid menthyl ester (menthyl anthranilate; Neo Heliopan® MA), 2,2',4,4'-tetrahydroxybenzophenone (benzophenone-2; Uvinul® D-50), 2,2'-dihydroxy-4,4'-dimethoxybenzophenone (benzophenone-6), 2,2'-dihydroxy-4,4'-dimethoxybenzophenone-5 sodium sulfonate and 2-cyano-3,3'-diphenylacrylic acid 2'-ethylhexyl ester. Preferred are 4-aminobenzoic acid, N,N,N-trimethyl-4-(2-oxoborn-3-ylidenemethyl)aniline methyl sulfate, 3,3,5-trimethylcyclohexyl salicylate, 2-hydroxy-4-methoxybenzophenone, 2-phenylbenzimidazole-5-sulfonic acid and its potassium, sodium and triethanolamine salts, 3,3'-(1,4-phenylenedimethylene)-bis(7,7-dimethyl-2-oxobicyclo[2.2.1]hept-1-yl-methanesulfonic acid) an its salts, 1-(4-tert-butylphenyl)-3-(4-methoxyphenyl)propane-1,3-dione, α-(2-oxoborn-3-ylidene)toluene-4-sulfonic acid and its salts, ethoxylated 4-aminobenzoic acid ethyl ester, 4-dimethylaminobenzoic acid 2-ethylhexyl ester, salicylic acid 2-ethylhexyl ester, 4-methoxycinnamic acid isopentyl ester, 4-methoxycinnamic acid 2-ethylhexyl ester, 2-hydroxy-4-methoxybenzophenone-5-sulfonic acid and its sodium salt, 3-(4'-methylbenzylidene)-D,L-camphor, 3-benzylidenecamphor, 4-isopropylbenzyl salicylate, 2,4,6-trianilino-(p-carbo-2'-ethylhexyl-1'-oxi)-1,3,5-triazine, 3-imidazol-4-yl acrylic acid and its ethyl ester, polymers of N-{(2 and 4)-[2-oxoborn-3-ylidenemethyl]benzyl}acrylique acid amide. Most especially preferred according to the invention are 2-hydroxy-4-methoxybenzophenone, 2-phenylbenzimidazole-5-sulfonic acid and their potassium, sodium and triethanolamine salts, 1-(4-tert-butylphenyl)-3-(4-methoxyphenyl)propane-1,3-dione, 4-methoxycinnamic acid 2-ethylhexyl ester and 3-(4'-methylbenzylidene)-D,L-camphor.

Such UV filters whose molar extinction coefficient at the absorption maximum is above 15,000, in particular above 20,000, are preferred.

It has also been found that with structurally similar UV filters, in many cases the water-insoluble compound has a higher effect with respect to water-soluble compounds that differ from it through one or more additional ionic groups within the scope of the teaching according to the invention. Water insoluble within the scope of the invention is understood to be UV filters which do not dissolve in water more than 1 wt % at 20° C., in particular no more than 0.1 wt %. In addition, these compounds should be soluble in the usual cosmetic oil components at room temperature in an amount of at least 0.1 wt %, in particular at least 1 wt %. Use of water-insoluble UV filters may therefore be preferred according to the invention.

According to another embodiment of the invention, UV filters having a cationic group, in particular a quaternary ammonium group are preferred.

These UV filters have the general structure U-Q.

The structure part U stands for a group that absorbs UV rays. This group may in principle be derived from the known UV filters mentioned above that are usable in the cosmetic field by replacing a group, usually a hydrogen atom, of the UV filter by a cationic group Q, in particular with a quaternary amino function.

Compounds from which the structure part U can derive include for example:
 substituted benzophenones,
 p-aminobenzoic acid esters,
 diphenylacrylic acid esters,
 cinnamic acid esters,
 salicylic acid esters,
 benzimidazoles and
 o-aminobenzoic acid esters.

Structural parts U which are derived from cinnamic acid amide or from N,N-dimethylaminobenzoic acid amide are preferred according to this invention.

The structure parts U may be selected in principle so that the absorption maximum of the UV filters may be in the UVA range (315-400 nm) as well as in the UVB range (280-315 nm) or in the UVC range (<280 nm). The UV filters with an absorption maximum in the UV range, in particular in the range from approximately 280 nm to approximately 300 nm are especially preferred.

In addition, the structure part U is preferably selected, also as a function of structure part Q, so that molar extinction coefficient of the UV filter at the absorption maximum is above 15,000, in particular above 20,000.

The structure part Q contains as the cationic group preferably a quaternary ammonium group. This quaternary ammonium group may in principle be connected directly to the structure part U, so that the structure part U represents one of the four substituents of the positively charged nitrogen atom. However, one of the four substituents on the positively charged nitrogen atom is preferably a group, in particular an alkylene group with two to six carbon atoms, which functions as a compound between the structure part U and the positively charge nitrogen atom.

Group Q advantageously has the general structure $(CH_2)_x$—$N^+R^1R^2R^3X^-$ in which x stands for an integer from 1 to 4, $R^1$ and $R^2$ independently of one another stand for $C_{1-4}$ alkyl groups, $R^3$ stands for a $C_{1-22}$ alkyl group or a benzyl group and $X^-$ stands for a physiologically tolerable anion. Within the scope of this general structure, x preferably stands for the number 3, $R^1$ and $R^2$ each stand for a methyl group and $R^3$ stands for either a methyl group or a saturated or unsaturated, linear or branched hydrocarbon chain with eight to 22 carbon atoms, in particular ten to eighteen carbon atoms.

Physiologically acceptable anions include, for example, inorganic anions such as halides, in particular chloride, bromide and fluoride, sulfate ions and phosphate ions as well as organic anions such as lactate, citrate, acetate, tartrate, methosulfate and tosylate.

Two preferred UV filters with cationic groups are the commercially available compounds cinnamic acid amidopropyltrimethylammonium chloride (Incroquat® UV-283) and dodecyldimethylaminobenzamidopropyldimethylammonium tosylate (Escalol® HP 610).

The inventive teaching of course also includes the use of a combination of several UV filters. Within the scope of this embodiment, the combination of at least one water-soluble UV filter with at least one UV filter having a cationic group is preferred.

The UV filters are usually present in amounts of 0.01-5 wt %, based on the total preparation for use. Amounts of 0.1-2.5 wt % are preferred.

In a special embodiment, the inventive agent also contains one or more substantive dyes. This makes it possible for the treated keratinic fiber not only to be structured temporarily when using the agent but at the same time to also be dyed. This may be desirable in particular when only a temporary dyeing, e.g. with striking fashion colors is desired, which can then be removed from the keratinic fiber again by simply washing.

Substantive dyes are usually nitrophenylenediamines, nitroaminophenols, azo dyes, anthraquinones or indophenols. Preferred substantive dyes include the compounds known by the international designations, i.e. brand names, HC Yellow 2, HC Yellow 4, HC Yellow 5, HC Yellow 6, HC Yellow 12, Acid Yellow 1, Acid Yellow 10, Acid Yellow 23, Acid Yellow 36, HC Orange 1, Disperse Orange 3, Acid Orange 7, HC Red 1, HC Red 3, HC Red 10, HC Red 11, HC Red 13, Acid Red 33, Acid Red 52, HC Red BN, Pigment Red 57:1, HC Blue 2, HC Blue 11, HC Blue 12, Disperse Blue 3, Acid Blue 7, Acid Green 50, HC Violet 1, Disperse Violet 1, Disperse Violet 4, Acid Violet 43, Disperse Black 9, Acid Black 1 and Acid Black 52 as well as 1,4-diamino-2-nitrobenzene, 2-amino-4-nitrophenol, 1,4-bis-(β-hydroxyethyl)amino-2-nitrobenzene, 3-nitro-4-(β-hydroxyethyl)aminophenol, 2-(2'-hydroxyethyl)amino-4,6-dinitrophenol, 1-(2'-hydroxyethyl)amino-4-methyl-2-nitrobenzene, 1-amino-4-(2'-hydroxyethyl)amino-5-chloro-2-nitrobenzene, 4-amino-3-nitrophenol, 1-(2'-ureidoethyl)-amino-4-nitrobenzene, 4-amino-2-nitrodiphenylamine-2'-carboxylic acid, 6-nitro-1,2,3,4-tetrahydroquinoxaline, 2-hydroxy-1,4-naphthoquinone, picramic acid and the salts thereof, 2-amino-6-chloro-4-nitrophenol, 4-ethylamino-3-nitrobenzoic acid and 2-chloro-6-ethylamino-1-hydroxy-4-nitrobenzene.

Cationic substantive dyes are preferred for use. Especially preferred here are (a) cationic triphenylmethane dyes such as Basic Blue 7, Basic Blue 26, Basic Violet 2 and Basic Violet 14, (b) aromatic systems substituted with a quaternary nitrogen group such as Basic Yellow 57, Basic Red 76, Basic Blue 99, Basic Brown 16 and Basic Brown 57, as well as (c) substantive dyes containing a heterocycle having at least one quaternary nitrogen atom as mentioned in claims 6 through 11 of EP A2 998 908, for example, to which reference is herewith made explicitly at this point.

Preferred cationic substantive dyes of group (c) include in particular the following compounds:

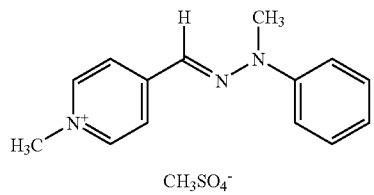
(DZ1)

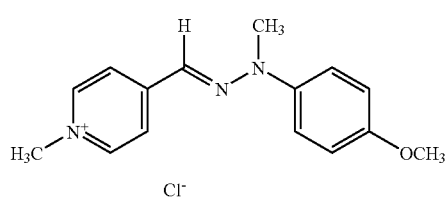
(DZ2)

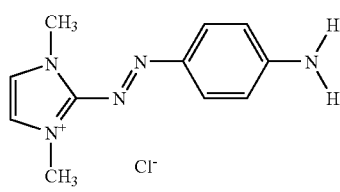
(DZ3)

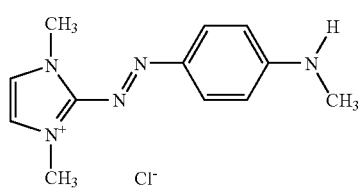
(DZ4)

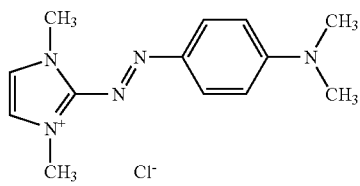
(DZ5)

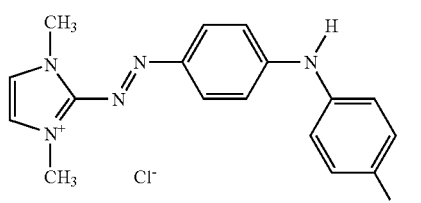
(DZ6)

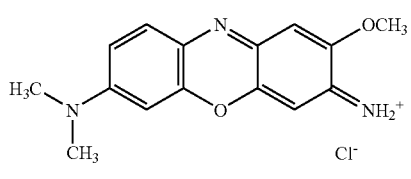
(DZ7)

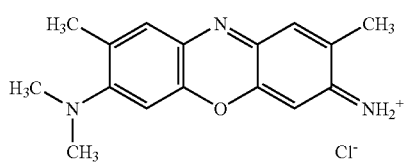
(DZ8)

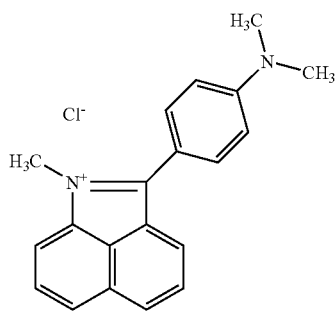
(DZ9)

The compounds of formulas (DZ1), (DZ3) and (DZ5), which are known by the designations Basic Yellow 87, Basic Orange 31 and Basic Red 51, are most especially preferred cationic substantive dyes of group (c).

The cationic substantive dyes distributed under the brand name Arianor® are also most especially preferred cationic substantive dyes according to the invention.

The inventive agents according to this embodiment preferably contain the substantive dyes in an amount of 0.001 to 20 wt %, based on the total agent.

In addition, the inventive agents may also contain naturally occurring dyes such as those contained in, for example, henna red, henna neutral, henna black, chamomile flowers, sandalwood, black tea, buckthorn bark, sage, logwood, madder root, catechu, sedre and alkanet root.

It is not necessary for each of the substantive dyes to be uniform compounds. Instead, due to the production process, other components may also be present in subordinate amounts in the inventive agents unless they have a negative effect on the styling result or must be excluded for other reasons, e.g. toxicological reasons.

The agents may also contain, in addition to the aforementioned components, all the active ingredients, additives and auxiliary substances known for such preparations.

Additional active ingredients, additives and auxiliary substances include, for example:
- thickeners such as agar, guar gum, alginates, xanthan gum, gum arabic, karaya gum, carob flower, linseed gums, dextrans, cellulose derivatives, e.g. methylcellulose, hydroxyalkylcellulose and carboxymethylcellulose, starch fractions and derivatives such as amylose, amylopectin and dextrans, clays, e.g. bentonite, fully synthetic hydrocolloids, e.g. polyvinyl alcohol and optionally crosslinked polyacrylates,
- structurizers, such as maleic acid and lactic acid,
- perfume oils, dimethyl isosorbide and cyclodextrins,
- solvents and solubilizers such as ethanol, isopropanol, ethylene glycol, propylene glycol, glycerol and diethylene glycol,
- quaternized amines such as methyl-1-alkylamidoethyl-2-alkylimidazolinium methosulfate,
- foam suppressants such as silicones,
- dyes for coloring the agent,
- antidandruff active ingredients such as piroctone olamine, zinc omadine and climbazole,
- substances to adjust the pH such as conventional acids, in particular edible acids and bases,
- cholesterol,
- consistency-imparting agents such as sugar esters, polyol esters or polyalkyl ethers,
- fats and waxes such as spermaceti, beeswax, montan wax and paraffins,
- fatty acid alkanolamides,
- complexing agents such as EDTA, NTA, β-alaninediacetic acid and phosphonic acids,
- swelling and penetration substances such as glycerol, propylene glycol monoethyl ether, carbonates, bicarbonates, guanidines, ureas and primary, secondary and tertiary phosphates,
- opacifiers such as latex, styrene/PEVP and styrene/acrylique acid amide copolymers,
- pearlizing agents such as ethylene glycol mono- and distearate as well as PEG-3 distearate,
- preservatives,
- stabilizers for hydrogen peroxide and other oxidizing agents,
- propellants such as propane-butane mixtures, $N_2O$, dimethyl ether, $CO_2$ and air,
- antioxidants.

With regard to other optional components as well as the amounts of these components used, reference is made explicitly to the relevant handbooks with which those skilled in the art are familiar.

The inventive agents may be formulated in all forms customary for styling agents, for example, in the form of solutions which may be applied as hair tonic or pump or aerosol sprays to the hair, in the form of creams, emulsions, waxes, gels or foaming solutions containing surfactants or other preparations suitable for application to hair.

Hair creams and hair gels usually contain structurizers and/or thickening polymers which serve to impart the desired consistency to the products, Structurizers and/or thickening polymers are typically used in an amount of 0.1 to 10 wt %, based on the total product. Amounts of 0.5 to 5 wt %, in particular 0.5 to 3 wt % are preferred.

The inventive agents are preferably finished as a pump spray, aerosol spray, pump hair mousse or aerosol hair mousse.

The term hair mousse is understood to refer to compositions which form a foam when removed from a suitable container. It may be necessary to add ingredients which promote foaming or stabilize the foam once it is formed to these agents, Surfactants and/or emulsifiers are suitable for this in particular.

If the inventive product is an aerosol product, it necessarily contains a propellant.

Propellants suitable according to the invention include, for example, $N_2O$, dimethyl ether, $CO_2$, air and alkanes with three to five carbon atoms, such as propane, n-butane, isobutane, n-pentane and isopentane and mixtures thereof. Preferred are dimethyl ether, propane, n-butane, isobutane and mixtures thereof.

According to a preferred embodiment, the aforementioned alkanes, mixtures of the aforementioned alkanes or mixtures of the aforementioned alkanes with dimethyl ether are used as the sole propellant. However, the invention also explicitly includes the joint use of propellants of the fluorochlorocarbon type, but in particular fluorocarbons.

With a given spray device, the size of the aerosol droplets and/or the foam bubbles and the respective size distribution can be adjusted through the quantity ratio of propellant to the other ingredients of the preparations.

The amount of propellant used varies as a function of the concrete composition of the agent, the packaging used and the desired type of product, e.g. hair spray or hair mousse. When using traditional spray devices, aerosol foam products preferably contain the propellant in amounts of 1 to 35 wt %, based on the total product. Amounts of 2 to 30 wt %, in particular from 3 to 15 wt % are especially preferred. Aerosol sprays generally contain larger amounts of propellant. In this case, the propellant is preferably used in an amount of 30 to 98 wt %, based on the total product. Amounts of 40 to 95 wt %, in particular 50 to 95 wt % are especially preferred.

The aerosol products can be produced in the usual way. As a rule, all the ingredients of the respective agent except for the propellant are filled into a suitable pressure-resistant container, which is then sealed with a valve. Finally, the desired amount of propellant is added by traditional techniques.

The inventive agents are particularly preferably finished as aerosol hair mousse.

A second subject matter of the invention is therefore aerosol hair mousse containing the inventive agent and at least one propellant.

Preferred inventive agents and propellants of the aerosol hair mousse as well as the respective amounts of propellant correspond to the description given above.

To promote foaming or to stabilize a foam once it is formed, the aerosol foams preferably contain at least one surfactant and/or one emulsifier.

Preferably a cationic surfactant is used such as that already described above as a suitable care substance. With regard to the preferred cationic surfactants and the amounts used, the statements made above apply accordingly.

In addition to or instead of the cationic surfactants, the aerosol foams may also contain other surfactants or emulsifiers, but in principle anionic, ampholytic and nonionic surfactants as well as all types of known emulsifiers are suitable. The group of ampholytic or amphoteric surfactants comprises zwitterionic surfactants and ampholytes. The surfactants may themselves have an emulsifying effect.

However, the aerosol foams preferably contain at least one cationic surfactant. The aerosol foams particularly preferably contain only cationic surfactants.

In principle, all anionic surfactant substances suitable for use on the human body are suitable as the anionic surfactant here. These are characterized by a water-solubilizing anionic group such as a carboxylate, sulfate, sulfonate or phosphate group and a lipophilic alkyl group with approximately 8 to 30 carbon atoms. In addition, glycol or polyglycol ether groups, ester, ether and amide groups as well as hydroxyl groups may be present in the molecule. Examples of suitable anionic surfactants include the following, each in the form of the sodium, potassium and ammonium salts as well as the mono-, di- and trialkanolammonium salts with two to four carbon atoms in the alkanol group:

linear and branched fatty acid with 8 to 30 carbon atoms (soaps), ether carboxylic acids of the formula R—O—(CH$_2$—CH$_2$O)$_x$—CH$_2$—COOH in which R is a linear alkyl group with 8 to 30 carbon atoms and x=0 or 1 to 16, acyl sarcosides with 8 to 24 carbon atoms in the acyl group, acyl taurides with 8 to 24 carbon atoms in the acyl group, acyl isethionates with 8 to 24 carbon atoms in the acyl group, sulfosuccinic acid mono- and dialkyl esters with 8 to 24 carbon atoms in the alkyl group and sulfosuccinic acid monoalkylpolyoxyethyl esters with 8 to 24 carbon atoms in the alkyl group and one to six ethoxy groups, linear alkanesulfonates with 8 to 24 carbon atoms, linear α-olefinsulfonates with 8 to 24 carbon atoms, α-sulfofatty acid methyl esters of fatty acids with 8 to 30 carbon atoms, alkyl sulfates and alkyl polyglycol ether sulfates of the formula R—O(CH$_2$—CH$_2$O)$_x$—OSO$_3$H, in which R is a preferably linear alkyl group with 8 to 30 carbon atoms and x=0 or 1 to 12, mixed surface-active hydroxysulfonates, sulfated hydroxyalkylpolyethylene and/or hydroxyalkylene propylene glycol ethers, sulfonated unsaturated fatty acids with 8 to 24 carbon atoms and one to six double bonds, esters of tartaric acid and citric acid with alcohols which are the addition products of approximately 2-15 molecules of ethylene oxide and/or propylene oxide onto fatty alcohols with 8 to 22 carbon atoms, alkyl and/or alkenyl ether phosphates of the formula (E1-I)

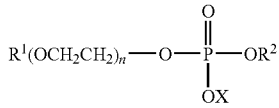

(E1-I)

in which R$^1$ preferably stands for an aliphatic hydrocarbon radical with 8 to 30 carbon atoms, R$^2$ stands for hydrogen, a (CH$_2$CH$_2$O)$_n$R$^1$ radial or X, n stands for numbers from 1 to 10 and X stands for hydrogen, an alkali or alkaline earth metal or NR$^3$R$^4$R$^5$R$^6$, where R$^3$ to R$^6$, independently of one another, stand for hydrogen or a C$_1$ to C$_4$ hydrocarbon radical, sulfated fatty acid alkylene glycol esters of formula (E1-II)

R$^7$CO(AlkO)$_n$SO$_3$M (E1-II)

in which R$^7$CO stands for a linear or branched, aliphatic, saturated and/or unsaturated acyl radical with 6 to 22 carbon atoms, Alk stands for CH$_2$CH$_2$, CHCH$_3$CH$_2$ and/or CH$_2$CHCH$_3$, n stands for numbers from 0.5 to 5 and M stands for a cation as described in Unexamined German Patent DE-OS 197 36 906, monoglyceride sulfates and monoglyceride ether sulfates of the formula (E1-III)

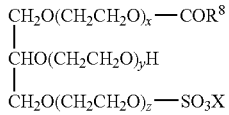

(E1-III)

in which R$^8$CO stands for a linear or branched acyl radical with 6 to 22 carbon atoms, x, y and z stand for a total of 0 or for numbers from 1 to 30, preferably 2 to 10 and X stands for an alkali or alkaline earth metal. Typical examples of monoglyceride (ether) sulfates suitable in the sense of the invention include the reaction products of lauric acid monoglyceride, coco fatty acid monoglyceride, palmitic acid monoglyceride, stearic acid monoglyceride, oleic acid monoglyceride and tallow fatty acid monoglyceride as well as their ethylene oxide adducts with sulfur trioxide or chlorosulfonic acid in the form of their sodium salts. Monoglyceride sulfates of the formula (E1-III) in which R$^8$CO stands for a linear acyl radical with 8 to 18 carbon atoms are preferred, amide ether carboxylic acids, condensation products of C$_8$-C$_{30}$ fatty alcohols with protein hydrolyzates and/or amino acids and their derivatives with which those skilled in the art are familiar as protein fatty acid condensates, for example, the Lamepon® types, Gluadin® types, Hostapon® KCG or the Amisoft® types.

Preferred anionic surfactants are alkyl sulfates, alkyl polyglycol ether sulfates and ether carboxylic acids with 10 to 18 carbon atoms in the alkyl group and up to 12 glycol ether groups in the molecule, sulfosuccinic acid monoalkyl and dialkyl ester with 8 to 18 carbon atoms in the alkyl group and sulfosuccinic acid monoalkylpolyoxyethyl esters with 8 to 18 carbon atoms in the alkyl group and one to 6 ethoxy groups, monoglyceride sulfates, alkyl and alkenyl ether phosphates as well as protein fatty acid condensates.

Zwitterionic surfactants are surface-active compounds which have in the molecule at least one quaternary ammonium group and at least one COO$^{(-)}$ or SO$_3^{(-)}$ group. Especially suitable zwitterionic surfactants include the so-called betaines such as N-alkyl-N,N-dimethylammonium glycinates, for example, cocoalkyldimethylammonium glycinate, N-acylaminopropyl-N,N-dimethylammonium glycinates, for example, cocoacylaminopropyldimethylammonium glycinate and 2-alkyl-3-carboxymethyl-3-hydroxyethylimidazolines each with 8 to 18 carbon atoms in the alkyl or acyl group as well as cocoacylaminoethyl-hydroxyethylcarboxymethyl glycinate. The fatty acid amide derivative known by the INCI designation cocamidopropylbetaine is a preferred zwitterionic surfactant.

Ampholytes are understood to be surface-active compounds which not only have a C$_8$-C$_{24}$ alkyl or acyl group in the molecule but also have a free amino group and at least one COOH or SO$_3$H group and are capable of forming internal salts. Examples of suitable ampholytes include N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids, each with approximately 8 to 24 carbon atoms in the alkyl group. Especially preferred ampholytes are N-cocoalkylaminopropionate, cocoacylaminoethylaminopropionate and C$_{12}$-C$_{18}$ acylsarcosine.

Nonionic surfactants contain as the hydrophilic group, for example, a polyol group, a polyalkylene glycol ether group or a combination of a polyol group and a polyglycol ether group. Such compounds include, for example:

addition products of 2 to 50 mol ethylene oxide and/or 1 to 5 mol propylene oxide onto linear and branched fatty alcohols with 8 to 30 carbon atoms, onto fatty acids with 8 to 30 carbon atoms and onto alkylphenols with 8 to 15 carbon atoms in the alkyl group, with end-group-capped (with a methyl radical or a C$_2$-C$_6$ alkyl radical) addition products of 2 to 50 mol ethylene oxide and/or 1 to 5 mol propylene oxide onto linear and branched fatty alcohols with 8 to 30 carbon atoms, onto fatty acids with 8 to 30 carbon atoms and onto alkylphenols with 8 to 15 carbon atoms in the alkyl group, such as those available under the brand names Dehydrol® LS, Dehydrol® LT (Cognis), $C_{12}$-$C_{30}$ fatty acid mono- and diesters of addition products of 1 to 30 mol ethylene oxide onto glycerol, addition products of 5 to 60 mol ethylene oxide onto castor oil and hardened castor oil, polyol fatty acid esters, for example, the commercial product Hydagen® HSP (Cognis) or Sovermol types (Cognis), alkoxylated triglycerides, alkoxylated fatty acid alkyl esters of formula (E4-I)

$$R^1CO—(OCH_2CHR^2)_wOR^3 \qquad (E4\text{-}I)$$

in which $R^1CO$ stands for a linear or branched, saturated or unsaturated acyl radical with 6 to 22 carbon atoms, $R^2$ stands for hydrogen or methyl, $R^3$ stands for linear or branched alkyl radicals with 1 to 4 carbon atoms, and w stands for numbers from 1 to 20, amine oxides, hydroxy mixed ethers such as those described in Unexamined German Patent DE-OS19738866, sorbitan fatty acid esters and addition products of ethylene oxide onto sorbitan fatty acid esters such as polysorbates, sugar fatty acid esters and addition products of ethylene oxide onto sugar fatty acid esters, addition products of ethylene oxide onto fatty acid alkanolamides and fatty amines, sugar surfactants of the alkyl and alkenyl oligoglycoside type according to formula (E4-II)

$$R^4O\text{-}[G]_p \qquad (E4\text{-}II)$$

in which $R^4$ stands for an alkyl or alkenyl radical with 4 to 22 carbon atoms, G stands for a sugar radical with 5 or 6 carbon atoms and p stands for numbers from 1 to 10. They may be obtained by the relevant methods of preparative organic chemistry.

The alkyl and alkenyl oligoglycosides may be derived from aldoses and/or ketoses with 5 or 6 carbon atoms, preferably from glucose. The preferred alkyl and/or alkenyl oligoglycosides are thus alkyl and/or alkenyl oligoglucosides. The index number p in the general formula (E4-II) indicates the degree of oligomerization (DP), i.e. the distribution of mono- and oligoglycosides and stands for a number between 1 and 10. Although p in the individual molecule must always be an integer and here may assume the values p=1 to 6 in particular, the value p for a specific alkyl oligoglycoside is a mathematical quantity determined analytically and usually represents a fractional number. Alkyl and/or alkenyl oligoglycosides with an average degree of oligomerization p of 1.1 to 3.0 are preferably used. From the standpoint of applications technology, such alkyl and/or alkenyl oligoglycosides whose degree of oligomerization is less than 1.7 and in particular is between 1.2 and 1.4 are preferred. The alkyl and/or alkenyl radical $R^4$ may be derived from primary alcohols with 4 to 11 carbon atoms, preferably 8 to 10 carbon atoms. Typical examples include butanol, hexyl alcohol, n-octyl alcohol, n-decyl alcohol and undecyl alcohol as well as technical-grade mixtures thereof such as those obtained from hydrogenation of technical-grade fatty acid methyl esters or in the course of hydrogenation of aldehydes from Roelen's oxosynthesis. Preferred are alkyl oligoglucosides of the chain length $C_8$-$C_{10}$ (DP=1 to 3) which are obtained as the first runnings in distillative separation of technical-grade $C_8$-$C_{18}$ coco fatty alcohol and may be contaminated with an amount of less than 6 wt % $C_{12}$ alcohol as well as alkyl oligoglucosides based on technical-grade $C_{9/11}$ oxo alcohols (DP=1 to 3). The alkyl and/or alkenyl radical $R^{15}$ may also be derived from primary alcohols with 12 to 22 carbon atoms, preferably 12 to 14 carbon atoms. Typical examples include lauryl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol as well as their technical-grade mixtures, which may be obtained as described above. Alkyl oligoglucosides based on hardened $C_{12/14}$ coco alcohol with a DP of 1 to 3 are preferred.

Sugar surfactants of the fatty acid N-alkylpolyhydroxyalkylamide type, a nonionic surfactant of the formula (E4-III)

$$R^5CO—\underset{\underset{R^6}{|}}{N}\text{-}[Z] \qquad (E4\text{-}III)$$

in which $R^5CO$ stands for an aliphatic acyl radical with 6 to 22 carbon atoms, $R^6$ stands for hydrogen, an alkyl or hydroxyalkyl radical with 1 to 4 carbon atoms and [Z] stands for a linear or branched polyhydroxyalkyl radical with 3 to 12 carbon atoms and 3 to 10 hydroxyl groups. The fatty acid N-alkylpolyhydroxyalkylamides are known substances which can usually be obtained by reductive amination of a reducing sugar with ammonia, an alkylamine or an alkanolamine and subsequent acylation with a fatty acid, a fatty alkyl ester or a fatty acid chloride. The fatty acid N-alkylpolyhydroxyalkylamides are preferably derived from reducing sugars with 5 or 6 carbon atoms, in particular from glucose. The preferred fatty acid N-alkylpolyhydroxyalkylamides are therefore fatty acid N-alkylglucamides as represent by the formula (E4-IV):

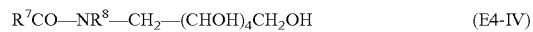

$$R^7CO—NR^8—CH_2—(CHOH)_4CH_2OH \qquad (E4\text{-}IV)$$

Glucamides of the formula (E4-IV), in which $R^8$ stands for hydrogen or an alkyl group and $R^7CO$ stands for the acyl radical of caproic acid, caprylic acid, capric acid, lauric acid, myristic acid, palmitic acid, palmoleic acid, stearic acid, isostearic acid, oleic acid, elaidic acid, petroselic acid, linoleic acid, linolenic acid, arachic acid, gadoleic acid, behenic acid or erucaic acid and/or technical-grade mixtures of these acids are preferred as the fatty acid N-alkylpolyhydroxyalkylamides. Especially preferred are fatty acid N-alkylglucamides of the formula (E4-IV), which are obtained by reductive amination of glucose with methylamine and subsequent acylation with lauric acid or $C_{12/14}$ coco fatty acid and/or a corresponding derivative. In addition, the polyhydroxyalkylamides may also be derived from maltose and palatinose.

The alkylene oxide addition products onto saturated linear fatty alcohols and fatty acids with 2 to 30 mol ethylene oxide per mol fatty alcohol and/or fatty acid have proven to be the preferred nonionic surfactants. Preparations with excellent properties are also obtained when they contain fatty acid esters of ethoxylated glycerol as nonionic surfactants.

These compounds are characterized by the following parameters. The alkyl radical R contains 6 to 22 carbon atoms and may be linear as well as branched. Primary linear aliphatic radicals and those with methyl branching in position 2 are preferred. Such alkyl radicals include, for example, 1-octyl, 1-decyl, 1-lauryl, 1-myristyl, 1-cetyl and 1-stearyl. Especially preferred are 1-octyl, 1-decyl, 1-lauryl, 1-myristyl. When using so-called oxo alcohols as starting materials, compounds with an odd number of carbon atoms in the alkyl chain are predominant.

In addition, the sugar surfactants may also be present as nonionic surfactants, These are preferably contained in amounts of 0.1 to 20 wt %, based on the respective total composition. Amounts of 0.5 to 15 wt % are especially preferred, and amounts of 0.5 to 7.5 wt % are most especially preferred.

The compounds with alkyl groups used as the surfactant may be uniform substances, but it is usually preferable to start with native plant or animal raw materials in production of these substances, so the result is substance mixtures having different chain lengths which depend on the respective raw material.

With the surfactants which are addition products of ethylene oxide and/or propylene oxide onto fatty alcohols or derivatives of these additional products, products with a "normal" homolog distribution as well as those with a narrow-range homolog distribution may be used. A "normal" homolog distribution is understood to be mixtures of homologs obtained in the reaction of fatty alcohols and alkylene oxide using alkali metals, alkali metal hydroxides or alkali metal alcoholates as the catalyst. However, narrow-range homolog distributions are obtained when using, for example, hydrotalcites, alkaline earth metal salts of ether carboxylic acids, alkaline earth metal oxides, hydroxides or alcoholates as catalysts. Use of products with a narrow-range homolog distribution may be preferred.

The additional surfactants are usually used in amounts of 0.1 to 45 wt %, preferably 0.5 to 30 wt % and most particularly preferably from 0.5 to 25 wt %, based on the respective total composition.

The aerosol foams may also contain at least one emulsifier. Emulsifiers act at the phase boundary to form water-stable and/or oil-stable adsorption layers which prevent the dispersed droplets from coalescing and thus stabilize the emulsion. Therefore, like surfactants, emulsifiers therefore have a hydrophobic molecular component and a hydrophilic molecular component. Hydrophilic emulsifiers preferentially form O/W emulsions, while hydrophobic emulsifiers preferentially form W/O emulsions. The choice of these emulsifying surfactants or emulsifiers depends on the substances to be dispersed and the respective external phase as well as how finely divided the emulsion is. Emulsifiers usable according to the invention include for example:

- Addition products of 4 to 100 mol ethylene oxide and/or 1 to 5 mol propylene oxide onto linear fatty alcohols with 8 to 22 carbon atoms, onto fatty acids with 12 to 22 carbon atoms and onto alkylphenols with 8 to 15 carbon atoms in the alkyl groups,
- $C_{12}$-$C_{22}$ fatty acid mono- and diesters of addition products of 1 to 30 mol ethylene oxide onto polyols with 3 to 6 carbon atoms, in particular onto glycerol,
- Ethylene oxide and polyglycerol addition products onto methyl glucoside fatty acid esters, fatty acid alkanolamides and fatty acid glucamides,
- $C_8$-$C_{22}$ alkyl mono- and oligoglycosides and their ethoxylated analogs, where degrees of oligomerization of 1.1 to 5, in particular 1.2 to 2.0, and glucose are preferred as the sugar component,
- Mixtures of alkyl(oligo)glucosides and fatty alcohols, for example, the commercially available product Montanov® 68,
- Addition products of 5 to 60 mol ethylene oxide onto castor oil and hardened castor oil,
- Partial esters of polyols with 3-6 carbon atoms with saturated fatty acids with 8 to 22 carbon atoms,
- Sterols. Sterols are understood to be a group of steroids having a hydroxyl group on carbon atom 3 of the steroid structure, isolated from animal tissue (zoosterols) as well as from vegetable fats (phytosterols). Examples of zoosterols include cholesterol and lanosterol. Examples of suitable phytosterols include ergosterol, stigmasterol and sitosterol. Sterols, so-called mycosterols, have also been isolated from fungi and yeasts.
- Phospholipids. This is understood to include mainly the glucose phospholipids, e.g. those obtained as lecithins and/or phosphatidylcholines, e.g. from egg yolk or plant seeds (e.g. soybeans).
- Fatty acid esters of sugars and sugar alcohols, such as sorbitol,
- Polyglycerols and polyglycerol derivatives, for example, polyglycerol poly-12-hydroxystearate (commercial product Dehymuls® PGPH),
- Linear and branched fatty acids with 8 to 30 carbon atoms and their sodium, potassium, ammonium, calcium, magnesium and zinc salts.

The emulsifiers are preferably used in amounts of 0.1 to 25 wt %, in particular 0.1 to 3 wt %, based on the respective total composition.

Nonionic emulsifiers with an HLB value of 8 to 18 according to the definitions given in *Römpp Lexikon Chemie* [Römpp's Lexicon of Chemistry] (eds. J. Falbe, M. Reglitz), 10$^{th}$ edition, Georg Thieme Verlag Stuttgart, New York (1997), page 1764 are preferred. Nonionic emulsifiers with an HLB value of 10 to 16 are especially preferred according to the invention.

A third subject matter of the invention is the use of the inventive agents for temporary deformation of keratinic fibers.

The inventive agents and products containing these agents, in particular aerosol hair mousse, are characterized in particular in that they impart a very strong and moisture-resistant styling hold to hair treated with them.

The hold of the shape, also known as the styling hold, as well as flexibility, elasticity and plasticity in the sense of the present invention are determined by the omega loop method.

To do so, a strand of dry hair (natural European hair from the company Kerling, Klebetresse [glued hair strand], thick, glued at one end, total length 150 mm, free length 130 mm, width 10 mm, weight 0.9±0.1 g) is placed for 30 seconds up to the lower edge of the adhesive in the polymer solution to be tested. Then the excess solution is rubbed off between the thumb and index finger, so that 0.5±0.02 g of the solution remains on the hair. The strands of hair saturated with the solution to be tested are wrapped around a Teflon cylinder with a diameter of 36 mm and the protruding ends are secured with a clip. The prepared strands are then dried and conditioned overnight at 25° C. and 50% relative atmospheric humidity or at 25° C. and 75% relative atmospheric humidity in a climate-controlled cabinet.

The conditioned strand is carefully removed from the Teflon cylinder. The resulting omega loop, a ring-shaped structure of hair stabilized in its shape by the polymer film thus formed, is clamped in a gripper attached to the measurement gauge and lowered until it is just above the bottom plate of an AMETEK LF Plus Universal Tester from the company AMETEK Precision Instruments Europe GmbH, Lloyd Product Group. The entire measurement is performed in a climate-controlled cabinet under constant climate conditions at 25° C. and 50% relative atmospheric humidity or at 25° C. and 75% relative atmospheric humidity.

To create standardized starting conditions, the measurement begins with approach to a preload of 0.1N at a rate of 30 mm·min$^{-1}$. Then the omega loop is compressed by 9 mm at the rate of 60 mm·min$^{-1}$ while the force required to do so is measured. After the characteristic force $F_1$ at the maximum deformation of 9 mm has been recorded, the strand is relaxed at the rate of 60 mm·min$^{-1}$ so that it is lifted 10 mm up from the bottom plate. From here the next cycle begins by again approaching the preload of 0.1N and next compressing the strand by 9 mm; the same rates are used here as those given above. The measurement of an omega loop includes a total of ten cycles.

With this measurement method, four characteristic parameters for describing the mechanical properties of film-forming polymers can be determined. Hold, flexibility, plasticity and elasticity can be calculated from the measured forces using the following formulas.

$$\text{Hold} = F_1 [N]$$

($F_1$ corresponds to the maximal force of the measurement)

$$\text{Flexibility} = F_{10}/F_1$$

(indicates the ratio of the maximal forces of the tenth cycle to the first cycle)

$$\text{Plasticity} = \frac{2 \cdot H_1 - H_{10}}{H_1}$$

(where $H_1 = 9$ mm and $H_{10} = 9$ mm + perfect plastic deformation of the strand)

$$\text{Elasticity} = \frac{\frac{F_{10}(2 \text{ mm}) - F_{10}(1.5 \text{ mm})}{0.5}}{\frac{F_1(2 \text{ mm}) - F_1(1.5 \text{ mm})}{0.5}} = \frac{E_{10}}{E_1}$$

(to calculate the elasticity, the forces for deformation of 1.5 mm and 2 mm are determined from the first and tenth cycles and then the ratio is formed).

The following examples are presented to illustrate the subject matter of the present invention without restricting it in any way.

EXAMPLES

The following quantitative amounts are understood to be given in percent by weight (wt %), unless other indicated.
1. Aerosol Foams The inventive agents E1 to E3 were prepared according to the following table.

| Raw materials | E1 | E2 | E3 |
|---|---|---|---|
| Sodium benzoate | 0.33 | 0.33 | 0.33 |
| Genamin CTAC[1] | 1.10 | 1.10 | 1.10 |
| PEG-40 hydrogenated castor oil[2] | 0.88 | 0.88 | 0.88 |
| Perfume | 0.11 | 0.11 | 0.11 |
| AMP-Ultra PC 1000[3] | 0.30 | 0.46 | 0.61 |
| Amphomer[4] | 1.65 | 2.50 | 3.25 |
| Luviquat Supreme[5] | 16.60 | 12.50 | 8.40 |
| Water, deionized | to 100 | to 100 | to 100 |

[1]Trimethylhexadecylammonium chloride (approximately 28-30% active substance in water; INCI designation: cetrimonium chloride) (Clariant)
[2]Hydrogenated castor oil with approximately 40-45 EO units (INCI designation: PEG-40 hydrogenated castor oil) (BASF)
[3]2-Amino-2-methylpropanol (INCI designation: aminomethyl propanol) (Dow Chemical)
[4]INCO designation: octylacrylique acid amide/acrylates/butylaminoethyl methacrylate copolymer
[5]Vinylpyrrolidone-methacrylique acid amide-vinylimidazole-vinylimidazolium-methosulfate copolymer (55:29:10:6) (19-21% solid in water; INCI designation: polyquaternium-68) (BASF)

To prepare aerosol hair mousse, these agents were each poured into a suitable pressure-resistant container, which was then closed with a valve. The agents were then mixed with a propellant mixture of propane and n-butane in a molar ratio of 1:1. The weight ratio of agent to propellant mixture was 92:8.
2. Proof of Effect Using the omega loop method (50% or 75% relative atmospheric humidity, 25° C.), the hold, the flexibility, the elasticity and the plasticity of various polymer solutions were determined. First, the polymer solutions P1 and P2 were tested and then a mixture of solutions P1 and P2 in a weight ratio of 1:1 was tested as polymer solution P3. The polymer solutions P1, P2 and P3 that were tested each contained 5 wt % polymer.

| Raw materials | P1 | P2 |
|---|---|---|
| AMP-Ultra PC 1000[3] | 0.82 | — |
| Amphomer[4] | 5.00 | — |
| Luviquat Supreme[5] | — | 25.00 |
| Water, deionized | to 100 | to 100 |

The result thus obtained and the values expected theoretically for polymer solution P3 (P3 (theoretical)) are listed in the following table:

| | P1 | P2 | P3 | P3 (theoretical) |
|---|---|---|---|---|
| Hold (cN) (50% relative atmospheric humidity) | 107 | 271 | 200 | 189 |
| Flexibility (%) (50% relative atmospheric humidity) | 72 | 87 | 75 | 79.5 |
| Elasticity (%) (50% relative atmospheric humidity) | 39 | 58 | 55 | 48.5 |
| Plasticity (%) (50% relative atmospheric humidity) | 10 | 7 | 10 | 8.5 |
| Hold (cN) (75% relative atmospheric humidity) | 90 | 211 | 234 | 150.5 |
| Flexibility (%) (75% relative atmospheric humidity) | 72 | 89 | 87 | 80.5 |
| Elasticity (%) (75% relative atmospheric humidity) | 35 | 68 | 54 | 51.5 |
| Plasticity (%) (75% relative atmospheric humidity) | 8 | 13 | 13 | 10.5 |

A comparison of the theoretical values determined mathematically for polymer solution P3 with the measurement results obtained shows clearly that the combination of amphoteric polymer A and copolymer B leads to a synergistic increase in hold. This effect is especially pronounced when the measurement is performed at a high atmospheric humidity. Thus, not only a strong hold but at the same also a moisture-resistant hold is achieved. Flexibility, elasticity and plasticity correspond at least to the expected values. To some extent a surprising improvement is also observed for these properties.

Testing of the inventive agents E1, E2 and E3 shows that high degrees of hold and also good values for flexibility, elasticity and plasticity are also obtained in the presence of other conventional ingredients for styling agents. The results of corresponding measurements by means of the omega loop method are given in the following table:

| | E1 | E2 | E3 |
|---|---|---|---|
| Hold (cN) (50% relative atmospheric humidity) | 186 | 217 | 242 |

-continued

|  | E1 | E2 | E3 |
|---|---|---|---|
| Flexibility (%) (50% relative atmospheric humidity) | 85 | 90 | 86 |
| Elasticity (%) (50% relative atmospheric humidity) | 67 | 69 | 60 |
| Plasticity (%) (50% relative atmospheric humidity) | 15 | 15 | 15 |

The invention claimed is:

1. An agent for temporary deformation of keratinic fibers, containing in a cosmetically acceptable carrier,
   a) N-octylacrylic acid amide/acrylic acid/tert-butylaminoethyl methacrylate copolymer as a polymer A and
   b) a copolymer B comprising
      a monomer B1 selected from acrylic acid amide, methacrylic acid amide, N-alkylacrylic acid amide and N-alkyl-methacrylic acid amide,
      a monomer B2 selected from N-vinyllactams,
      a monomer B3 selected from quaternized N-vinylimidazoles and
      the monomer N-vinylimidazole.

2. The agent of claim 1, wherein the polymer A comprises 0.01 to 20 wt % of the total agent.

3. The agent of claim 1, wherein the monomer B1 is selected from acrylic acid amide and methacrylic acid amide.

4. The agent of claim 1, wherein the monomer B2 is selected from N-vinylcaprolactam and N-vinylpyrrolidone.

5. The agent of claim 1, wherein the monomer B3 is selected from 3-alkyl-1-vinylimidazolium salts with physiologically acceptable anions.

6. The agent of claim 5, wherein monomer B3 is 3-methyl-1-vinylimidazolium methyl sulfate.

7. The agent of claim 1, wherein copolymer B comprises
   a monomer B1 selected from acrylic acid amide and methacrylic acid amide,
   a monomer B2 selected from N-vinylcaprolactam and N-vinylpyrrolidone,
   3-methyl-1-vinylimidazolium methyl sulfate and
   N-vinylimidazole.

8. The agent of claim 1, wherein copolymer B comprises 0.01 to 20 wt % of the total agent.

9. The agent of claim 1, wherein the polymer A and the copolymer B are in a weight ratio of 1:20 to 20:1.

10. The agent of claim 1, wherein the agent further comprises a silicone oil or one silicone gum.

11. The agent of claim 10, wherein the silicone oil or silicone gum is selected from the group consisting of cyclic and linear polydialkylsiloxanes, alkoxylated cyclic and linear polydialkylsiloxanes and derivatives thereof, aminated cyclic and linear polydialkylsiloxanes and derivatives thereof, dihydroxypolydimethylsiloxanes and polyphenylalkylsiloxanes.

12. A method for the temporary shaping of hair comprising application of the agent of claim 1 to the hair.

13. An aerosol hair mousse comprising the agent of claim 1 and a propellant.

14. The agent of claim 1, wherein the polymer A comprises 0.1 to 15 wt % of the total agent.

15. The agent of claim 1, wherein the polymer A comprises 1.0 to 10 wt % of the total agent.

16. The agent of claim 1, wherein the copolymer B comprises 0.1 to 5 wt % of the total agent.

17. The agent of claim 1, wherein the polymer A and the copolymer B are in a weight ratio of 1:10 to 10:1.

18. The agent of claim 1, wherein the polymer A and the copolymer B are in a weight ratio of 1:3 to 3:1.

* * * * *